United States Patent [19]

Yaso et al.

[11] Patent Number: 5,001,237
[45] Date of Patent: * Mar. 19, 1991

[54] 2-SUBSTITUTED ALKOXY-3-SUBSTITUTED-PYRAZINES

[75] Inventors: Masao Yaso; Yukio Suzuki; Kensuke Shibata; Daisuke Mochizuki; Eiichi Hayashi, all of Shizuoka, Japan

[73] Assignee: Toyo Jozo Kabushiki Kaisha, Shizuoka, Japan

[*] Notice: The portion of the term of this patent subsequent to Jan. 16, 2007 has been disclaimed.

[21] Appl. No.: 381,958

[22] Filed: Jul. 19, 1989

Related U.S. Application Data

[62] Division of Ser. No. 68,228, Jun. 30, 1987, Pat. No. 4,894,453.

[30] Foreign Application Priority Data

Jun. 30, 1986 [JP] Japan .................. 61-153742
Jun. 30, 1986 [JP] Japan .................. 61-153743

[51] Int. Cl.$^5$ .................................. C07D 241/18
[52] U.S. Cl. ................................ 540/575; 540/598; 544/120; 544/357; 544/408
[58] Field of Search ............ 544/408, 357, 120; 540/598, 575

[56] References Cited

U.S. PATENT DOCUMENTS 3,787,411 1/1974 Ruschig .................. 544/408
4,560,756 12/1985 Brunnmueller ........... 544/408

Primary Examiner—Robert Gerstl
Attorney, Agent, or Firm—Young & Thompson

[57] ABSTRACT

A compound of the formula

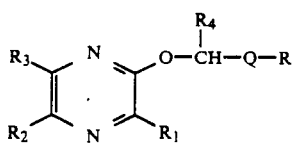

wherein Q is —CO— or —CH$_2$—, R is hydroxyl, lower alkoxy, halogen, —NH-lower alkylene-OH, —NH-lower alkylene-arylthio, —NH-lower alkylene-halogen,

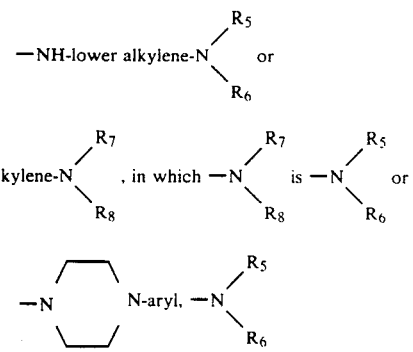

is dilower alkylamino, cycloalkylamino, morpholino,

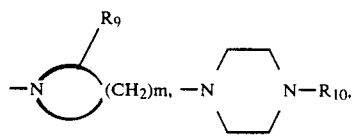

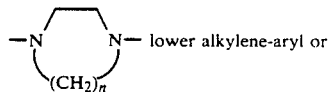

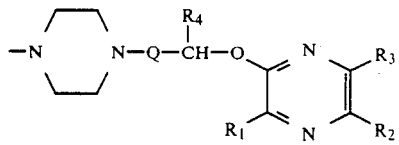

in which R$_9$ is hydrogen, lower alkyl or aryl, R$_{10}$ is hydrogen, lower alkyl, hydroxy-lower alkyl, hydroxy-lower alkoxy-lower alkyl or di(aryl)-lower alkyl, m is an integer from 4 to 6, n is 2 or 3, R$_1$ is alkyl or aryl-lower alkyl, R$_2$ and R$_3$ are each lower alkyl, or together form tetramethylene, and R$_4$ is hydrogen, lower alkyl or aryl, in which aryl is phenyl which is optionally substituted with a group selected from the group consisting of 1-3 halogen, nitro, lower alkyl and lower alkoxy, or a pharmaceutically acceptable salt thereof, inhibits blood platelet aggregation, has vasodilating activity and inhibits lipoperoxide generation.

2 Claims, No Drawings

2-SUBSTITUTED ALKOXY-3-SUBSTITUTED-PYRAZINES

This application is a division of application Ser. No. 07/068,228 filed June 30, 1987, now U.S. Pat. No. 4,894,453.

FIELD OF THE INVENTION

This invention relates to novel 2-substituted alkoxy-3-substituted pyrazines, which are useful as pharmaceuticals for treating circulatory and metabolic disorders. The compounds of the invention are active as platelet aggregation inhibiting, vasodilating and/or anti-lipoperoxide generating agents.

KNOWN PRIOR ART

Recently, a significant number of compounds having platelet aggregation inhibiting activity have been reported. Of these, the only known compounds having a pyrazine or 5,6,7,8-tetrahydro quinoxaline ring as the basic structure are tetramethyl pyrazine (16th Heterocyclic Chemistry Symposium (Osaka), pp. 65–68 (1984)) and 2-higher fatty acid acyloxymethyl pyrazine (Jap. Pat. Unexam. Publ. No. 59-219269). Furthermore, a compound of the formula

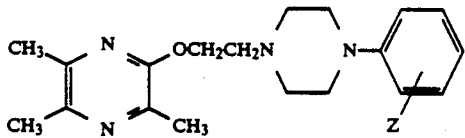

wherein Z is hydrogen or methyl, is known as an α-sympathetic nerve blocking agent (Jap. Pat. Exam. Publ. No. 48-21949). These compounds have almost no platelet aggregation inhibiting, vasodilating or antioxidant activity.

OBJECT OF THE INVENTION

It is an object of the invention to provide high quality pharmaceuticals having stronger inhibitory activities for platelet aggregation, in order effectively to treat circulation and metabolic disorders.

SUMMARY OF THE INVENTION

We have found that 2-substituted alkoxy-3-substituted pyrazines display inhibitory action on platelet aggregation, vasodilation activity and/or anti-lipoperoxide generation, and are expected to have excellent pharmaceutical properties.

According to the present invention, a compound of the formula

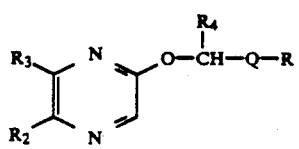 [1]

is provided, wherein Q is —CO— or —CH$_2$—, R is hydroxyl, lower alkoxy, halogen, —NH-lower alkylene-OH, —NH-lower alkylene-arylthio, —NH-lower alkylene-halogen,

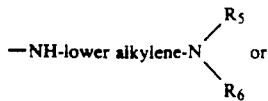

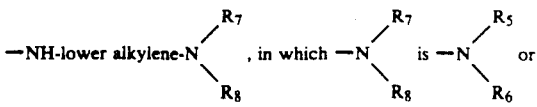

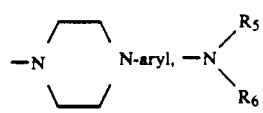

is dilower alkylamino, cycloalkylamino, morpholino,

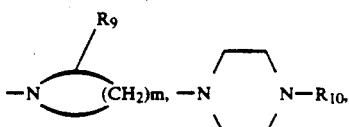

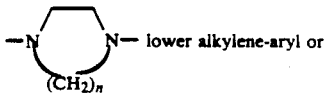

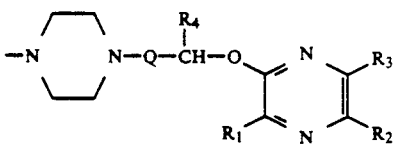

in which R$_9$ is hydrogen, lower alkyl or aryl, R$_{10}$ is hydrogen, lower alkyl, hydroxy-lower alkyl, hydroxy-lower alkoxy-lower alkyl or di(aryl)-lower alkyl, m is an integer from 4 to 6, n is 1 or 2, R$_1$ is alkyl or aryl-lower alkyl, R$_2$ and R$_3$ are each lower alkyl, or together form tetramethylene, and R$_4$ is hydrogen, lower alkyl or aryl, in which aryl is phenyl which is optionally substituted with a group selected from the group consisting of 1–3 halogen, nitro, lower alkyl and lower alkoxy, or a pharmaceutically acceptable salt thereof.

Compound [1] can be provided in salt form. The salts must be pharmacologically acceptable non-toxic salt thereof. Examples of such salts are salts of an inorganic acid such as hydrochloric, sulfuric, or phosphoric, and salts of an organic acid such as acetic, propionic, butyric, glycolic, gluconic, malic, tartaric, succinic, mandelic, aspartic, glutamic, methanesulfonic or toluenesulfonic. Salts of other known acids can be used as well.

Compound [1] can be produced by the following processes:

Process A

A process for the production of compound [1] wherein Q is —CO— and R is lower alkoxy (hereinafter designated as compound [1a]):

The above compound [1a] can be produced by reacting a compound of the formula

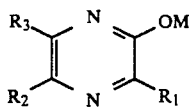 [3]

wherein M is alkali metal, and $R_1$, $R_2$ and $R_3$ have the same meanings hereinbefore, with an α-halogen-carboxylate ester of the formula

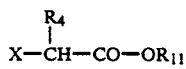 [4]

wherein X is halogen, $R_{11}$ is lower alkyl and $R_4$ has the same meaning hereinbefore, in an organic solvent.

The above compound [3] can be obtained by dissolving a compound of the formula

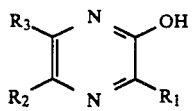 [2]

wherein $R_1$, $R_2$ and $R_3$ have the same meanings hereinbefore, in methanol containing alkali metal methylate and distilling off methanol in vacuo.

The above compound [2] can be expressed as a tautomer of a compound of the formula

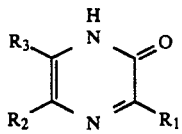

wherein $R_1$, $R_2$ and $R_3$ have the same meanings hereinabove.

In compound [2] above, $R_1$ is alkyl or aryl-lower alkyl. "Alkyl", as used above, is defined as saturated or unsaturated $C_{1-20}$ alkyl, which may be branched or unbranched. Examples are methyl, ethyl, propyl, isopropyl, butyl, isobutyl, sec-butyl, t-butyl, pentyl, isopentyl, hexyl, heptyl, octyl, nonyl, decyl, undecyl, dodecyl, tridecyl, tetradecyl, pentadecyl or hexadecyl, "Optionally substituted phenyl", as used above, is defined as phenyl or phenyl substituted with $C_{1-3}$ lower alkyl, halogen, nitro, or lower alkxoy. Aryl-lower alkyl, as used above, is defined as phenyl or phenyl substituted with 1-3 halogen, nitro, lower alkyl or lower alkoxy, in which lower alkyl means $C_{1-4}$ alkyl such as methyl, 1-ethyl, 2-ethyl, 3-propyl or 1-propyl. Examples are benzyl, p-chlorobenzyl, 2-phenylethyl and 1-phenylethyl.

In compound [2] above, $R_2$ and $R_3$ are each lower alkyl, or together form tetramethylene. The lower alkyl can be $C_{1-4}$ alkyl such as methyl, ethyl or propyl. Among the class of compounds [2], some examples have been reported. These compounds can be produced by a process or an improvement thereto as disclosed in *J. Am. Chem. Soc.*, 71:78–81 (1949) and ibid. 74:1580–1583 (1952). Novel derivatives thereof can also be produced according to the methods described in the above references. The compound [2] wherein $R_2$ and $R_3$ together form tetramethylene of the formula

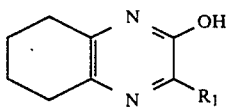 [2']

wherein $R_1$ has the same meaning hereinabove, hexahydroquinoxaline derivatives, is produced by the process, in which an α-amino acidamide of the formula

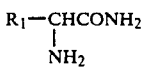

wherein $R_1$ has the same meaning hereinabove, is reacted with 1,2-cyclohexanedione in an alkaline medium.

The reaction of the above α-amino acidamide or a salt thereof with 1,2-cyclohexanedione proceeds in an organic solvent, for example a lower alcohol such as methanol or ethanol. The condensation reaction proceeds preferably below 0° C. at first; however, as the reaction proceeds, it can be effected at room temperature. The progress of the reaction can be checked by thin layer chromatography (hereinafter TLC) or high performance liquid chromatography (hereinafter HPLC) and is terminated upon reaching maximum production.

Isolation of the product [2'] can be performed by neutralizing the reaction mixture with an acid such as hydrochloric acid or sulfuric acid, thereafter extracting with water immiscible organic solvent such as chloroform under weakly alkaline conditions, and recrystallizing from an organic solvent such as acetone.

The thus-obtained product [2'] can be purified if necessary, by column chromatography using silica-gel, active alumina or an adsorption resin.

The group $R_4$ in the above α-halogenocarboxylate ester [4] is defined as hydrogen, lower alkyl or aryl. Examples of lower alkyl are $C_{1-4}$ alkyls such as methyl, ethyl or propyl, and that of aryl are phenyl optionally substituted with 1-3 halogen, nitro, lower alkyl or lower alkoxy.

The group $R_9$ in the above ester [4] is $C_{1-4}$ alkyl such as methyl, ethyl or propyl and the group X is halogen, such as chlorine, bromine or iodine.

The reaction of the compound [3] with an α-halogeno carboxylate ester [4] is in general effected in an organic solvent such as dimethylforamide while heating. Isolation of the product [1a] can be performed by distilling off the reaction solvent and extracting the residue with a water-immiscible organic solvent such as benzene chloroform.

Process B

A process for the production of compound [1] wherein Q is —CO— and R is hydroxyl (hereinafter compound [1b]):

Compound [1b] can be produced by de-esterifying the above compound [1a] by any known de-esterification procedure. For example, compound [1a] is hydrolyzed by alkali hydroxide such as KOH or NaOH, and in case any unreacted compound [1a] remains, after removing the same by extracting with a water-immiscible organic solvent such as chloroform, the reaction mixture is neutralized with an acid and the precipitated product [1b] is filtered or extracted with a water-immiscible organic solvent.

Process C

A process for the production of compound [1] wherein Q is —CO— and R is —NH-lower alkylene-OH or

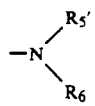

(hereinafter compound [1c]):

Compound [1c] can be produced by reacting an amine of the formula

H—R'  [5]

wherein R' is —NH-lower alkylene-OH or

, in which 

is di-lower alkylamino, cycloalkylamino morpholino,

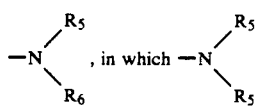

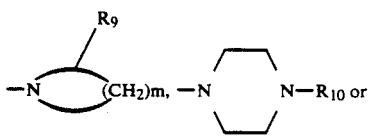

wherein $R_9$, $R_{10}$, aryl, m and n have the same meanings hereinbefore, with a compound [1b] or its reactive derivatives for N-acylation.

In the group R' in the above amine [5] the lower alkylene moiety is defined as straight or branched $C_{1-4}$ lower alkylene.

Examples of lower alkylene are methylene, ethylene, methylmethylene, propylene, 1-methylethylene, ethylmethylene butylene, isobutylene or sec-butylene; $C_{1-3}$ is preferred.

Di-lower alkylamino in the above

is dialkylamino of $C_{1-4}$ alkyl such as dimethylamino, diethylamino or dipropylamino.

The above cycloalkylamino is cycloalkylamino of $C_{5-8}$, cycloalkyl such as cyclopentylamino, cyclohexyamino or cycloheptylamino.

The ring

in the above

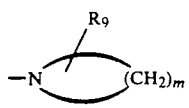

wherein m is an integer of 4–6, is defined as pyrrolidine, piperidine or a hexamethyleneimine ring, $R_9$ means hydrogen, lower alkyl or aryl. "Lower alkyl" means branched or unbranched $C_{1-4}$ alkyl. "Aryl" as used above means phenyl or phenyl substituted with 1–3 halogen, nitro, lower alkyl or lower alkoxy.

The group $R_{10}$ in the above

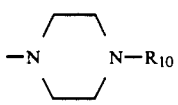

is defined as hydrogen, lower alkyl, hydroxy-lower alkyl, aryl, hydroxy-lower alkoxy-lower alkyl or di(aryl)-lower alkyl. Examples of the above alkyl are branched or unbranched $C_{1-4}$ alkyl such as methyl, ethyl, propyl, isopropyl, butyl, isobutyl, sec-butyl and t-butyl. Examples of the above hydroxy-lower alkyl are hydroxyalkyl of $C_{1-4}$ such as hydroxymethyl, 2-hydroxyethyl or 3-hydroxypropyl. Examples of hydroxy-lower alkoxy-lower alkyl are hydroxy alkoxy alkyl comprising alkoxy which is $C_{1-4}$ lower alkoxy and alkyl which is $C_{1-4}$ lower alkyl, for example hydroxymethoxymethyl, (2-hydroxyethoxy) methyl, 2-(2-hydroxyethoxy) ethyl or 2-(hydroxymethoxy) ethyl. The group "aryl" in the above di-(aryl)-lower alkyl is phenyl optionally substituted with 1–3 halogen, nitro, lower alkyl or lower alkoxy, and the group "lower alkyl" hereinabove is $C_{1-4}$ alkyl such as methyl or ethyl. An example of di-(aryl)-lower alkyl is diphenylmethyl.

The ring of the group

in the above

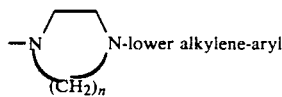

wherein n is 2 or 3, is piperazine or homopiperazine. A lower alkylene bound to the above ring is defined hereinabove and is branched or unbranched $C_{1-4}$ alkylene.

Examples of aryl are phenyl or phenyl substituted with 1–3 halogen, nitro, lower alkyl or lower alkoxy, such as phenyl, tolyl, xylyl, p(m or o)-chlorophenyl, p(m or o)-fluorophenyl, p(m or o)-bromophenyl, 2,4(2,3-, 3,4-, 2,5-, 3,5- or 2,6-)dichlorophenyl, p(m or o)-nitrophenyl, p(m or o)-methoxyphenyl, 2,4(2,3-, 3,4-, 2,5-, 3,5- or 2,6)-dimethoxyphenyl.

Accordingly, specific examples of the amine [5] are dimethylamine, diethylamine, 2-hydroxyethylamine, cyclohexylamine, morpholine, pyrrolidine, piperizine, hexamethyleneimine, 4-methylpiperizine, 4-phenylpiperazine, piperazine, 4-methylpiperazine, 4-ethylpiperazine, 4-propylpiperazine, 4-butylpiperazine, 4-(2-hydroxyethyl)-piperazine, 4-[2-(2-hydroxyethoxy)ethyl]-piperazine, 4-benzylpiperazine, 4-(o-chlorobenzyl)-piperazine, 4-(p-chlorobenzyl)-piperazine, 4-(2,4-dichlorobenzyl)-piperazine, 4-(p-nitrobenzyl)-piperazine, 4-(m-nitrobenzyl)-piperazine, 4-(o-nitrogenzyl)-piperazine, 4-(p-methoxybenzyl)-piperazine, 4-(methylbenzyl)-piperazine, 4-(diphenylmethyl)-piperazine, 4-benzyl-homopiperazine, 4-(p-methylbenzyl)-homopiperazine, 4-(p-chlorobenzyl)-homopiperazine, 4-(p-fluorobenzyl)-homopiperazine, 4-(p-nitrobenzyl)-homopiperazine and 4-(p-methoxybenzyl)-homopiperazine.

The reaction of the above amine [5] and the compound [1b] or its reaction derivative ordinarily proceeds by mixed anhydride method reacting the compound [1b] and amine [5] with pivaloyl chloride in the presence of a tertiary amine such as tetrahydrofuran.

The resulting compound [1f] can be isolated by pouring the reaction mixture into dilute aqueous alkali and extracting with a water-immiscible organic solvent such as benzene or chloroform.

In the above reaction, when piperazine is used as amine [5], a compound [1c], wherein R is

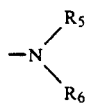

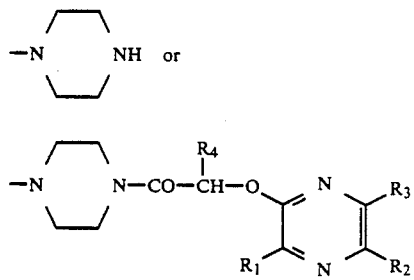

in
which $R_1$, $R_2$, $R_3$ and $R_4$ have the same meanings hereinbefore, is produced depending on a ratio of piperazine used.

Process D

A process for the production of the compound [1] wherein Q is —CO— and R is NH-lower alkylene-halogen (hereinafter compound [1d]):

Compound [1d] can be produced by N-acylating a compound of the formula

X-lower alkylene-NH₂      [6]

wherein X is halogen and lower alkyl has the same meaning hereinabove, with compound [1b] or a reactive derivative thereof.

"Lower alkylene" in the above amine [6] means, as defined hereinbefore, branched or unbranched $C_{1-4}$ alkylene, such as methylene, ethylene, methylmethylene, propylene, 1-methylethylene, ethylmethylene, butylene, isobutylene or sec-butylene, and —(CH$_2$)$_{1-3}$ is preferred.

Examples of the above amine [6] are 2-chloroethylamine and 2-bromoethylamine.

The reaction of the above amine [6] with the compound [1b] or its reactive derivative is performed in the same way as in the process C hereinabove to produce the compound [1d].

Process E

A process for the production of compound [1] wherein Q is —CO— and R is

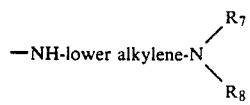

(hereinafter compound [1e]):

Compound [1e] can be produced by aminating the above compound [1d] with an amino of the formula

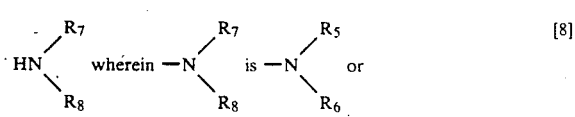

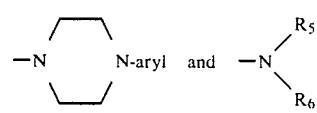

has the same meaning hereinbefore.
The group

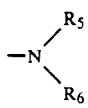

in the above amine [7] has the same meaning as

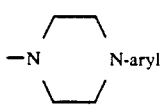

as defined in the above amine [5], and the group aryl as defined in the above

means phenyl or phenyl substituted with 1-3 halogen, nitro, lower alkyl or lower alkoxy.

Examples of amine [7] are the amine [5] hereinbefore and 4-phenylpiperazine, 4-(o-chlorophenyl)-piperazine, 4-(p-chlorophenyl)-piperazine, 4-(p-methoxyphenyl)-piperazine, 4-(m-methoxyphenyl)-piperazine or 4-(m-methoxyphenyl)-piperazine.

The above amination reaction can be effected in an inert organic solvent such as benzene in the presence of a tertiary organic amine such as triethylamine. Isolation of the product [1d] can be performed by pouring the reaction mixture into dilute aqueous alkali and extracting with a water-immiscible organic solvent such as chloroform.

Process F

A process for the production of compound [1] wherein Q is —CH$_2$— and R is —NH-lower alkylene-arylthio (hereinafter compound [1f]):

The above compound [1f] can be produced by thioetherification of the above compound [1d] with aryl-thiol [8].

Aryl in the above aryl-thiol [8] means phenyl or phenyl substituted with 1-3 halogen, nitro, lower alkyl or lower alkoxy, such as thiophenol.

The above thio-etherification can be effected in a reaction solvent such as dimethylformamide in the presence of an alkali such as potassium carbonate or sodium carbonate. Isolation of the compound [1f] can be performed by removing the reaction solvent and extracting with a water-immiscible organic solvent such as chloroform in a dilute aqueous alkali.

Process G

A process for the production for compound [1] wherein Q is —$CH_2$— and R is hydroxyl (hereinafter compound [1g]):

Compound [1g] can be produced by reducing the above compound [1a] with alkali borohydride in lower alcohol with heating.

Isolation of the product [1g] can be performed by removing the organic solvent from the reaction, adding water to the residue and extracting with a water-immiscible organic solvent such as chloroform.

Process H

A process for the production of compound [1] wherein Q is —$CH_2$— and R is halogen (hereinafter compound [1h]):

Compound [1h] can be produced by halogenating the above compound [1g] with a halogenating agent in a reaction solvent.

The said halogenating agent may be any known halogenating agent. Conventional chlorination reagents such as $SOCl_2$, $PCl_5$ and $POCl_3$ can be used. The halogenation reaction can be effected, in general, in an inert organic solvent such as chloroform. The reaction proceeds at room temperature. Isolation of the product [1h] can be performed by adding a water-immiscible organic solvent such as chloroform, washing with dilute aqueous alkali, dehydrating the organic layer and removing the solvent therefrom.

The resulting compound [1h] can be used without purification, as by silica-gel column chromatography, to derive compound [1j] below from compound [1h].

Process J

A process for production of compound [1] wherein Q is —$CH_2$— and R is

(hereinafter compound [1j]):

A compound [1j] can be produced by aminating compound [1h] above with the amine [5] in a reaction solvent with heating.

The above amination reaction can be effected in an organic solvent such as benzene with heating In the above reaction, co-generated acid can be removed by an acid binder, for example a known tertiary organic amine such as triethylamine.

The product [1j] can be isolated by pouring the reaction mixture into dilute aqueous alkali and extracting with a water-immiscible organic solvent such as benzene or chloroform.

The thus-obtained compound [1] is purified, if required, by column chromatography using silica gel, activated alumina or an adsorption resin with an elution solvent such as chloroform-methanol or benzene-ethyl acetate.

A compound [1] is generally produced in the form of its free base, but it can also be produced in the form of a conventional salt thereof. For example, a hydrochloride can be prepared by dissolving a compound [1] in a lower alcohol such as methanol or ethanol, adding a slight molar excess of hydrochloric acid, and isolating the precipitated material, or if not precipitated, by adding ether therein to precipitate the same. The molar ratio of hydrochloric acid may be different according to the specific compound [1].

Examples of the compound [1] of the present invention are set forth in Tables 1 and 2.

TABLE 1

$$R_3 \underset{R_2}{\overset{N}{\diagdown}} \underset{N}{\diagup} \overset{R_4}{\underset{R_1}{\diagdown}} O-CH-Q-R$$

| Compound No. | $R_1$ | $R_2$ | $R_3$ | $R_4$ | Q | R |
|---|---|---|---|---|---|---|
| 034 | Me | Me | Me | H | —CO— | —OMe |
| 035 | Me | Me | Me | Me | —CO— | —OMe |
| 036 | Me | Me | Me | Ph | —CO— | —OMe |
| 037 | Me | Me | Me | H | —CO— | —OH |
| 038 | Me | Me | Me | Me | —CO— | —OH |
| 039 | Me | Me | Me | Ph | —CO— | —OH |
| 066 | Me | Me | Me | H | —CO— | —N◯N—Me |
| 067 | Me | Me | Me | H | —CO— | —N◯$CH_2$ |

TABLE 1-continued structure: R3, R2 on pyrazine with N; O-CH(R4)-Q-R; R1

| Compound No. | R₁ | R₂ | R₃ | R₄ | Q | R |
|---|---|---|---|---|---|---|
| 068 | Me | Me | Me | H | —CO— | piperazin-N-CH₂CH₂—OH |
| 069 | Me | Me | Me | H | —CO— | —NH—CH₂CH₂—OH |
| 070 | Me | Me | Me | H | —CO— | piperazin-N-CO-CH₂-O-(2,5,6-trimethylpyrazinyl) |
| 071 | Me | Me | Me | H | —CO— | —NH—CH₂CH₂—NMe₂ |
| 072 | Me | Me | Me | H | —CO— | —NH—CH₂CH₂—S—Ph |
| 073 | Me | Me | Me | H | —CO— | —NH—CH₂CH₂—N(morpholino) |
| 074 | Me | Me | Me | H | —CO— | —NH—CH₂CH₂—N(azetidinyl)CH₂ |
| 075 | Me | Me | Me | H | —CO— | morpholino (—N O) |
| 076 | Me | Me | Me | H | —CO— | —NH—CH₂CH₂—N(piperazin)N—CH₂CH₂—OH |
| 103 | Me | Me | Me | H | —CO— | —NH—CH₂CH₂—N(piperazin)NH |
| 105 | Me | Me | Me | H | —CO— | —NH—CH₂CH₂—N(piperazin)N—Me |
| 135 | Me | Me | Me | H | —CO— | —NH—CH₂CH₂—N(piperazin)N—CH₂Ph—Cl (p) |
| 136 | Me | Me | Me | H | —CO— | —NH—CH₂CH₂—N(piperazin)N—CH₂Ph |
| 137 | Me | Me | Me | H | —CO— | —NH—CH₂CH₂—N(piperazin)N—CH₂Ph—Cl (o) |
| 341 | Et | Me | Me | Ph | —CO— | —NH—CH₂CH₂—N(morpholino)O |
| 342 | Et | Me | Me | Ph | —CO— | —NH—CH₂CH₂—N(piperazin)N—CH₂Ph |

TABLE 1-continued

Structure:
R₃, R₂ on pyrazine ring with N's, O—CH(R₄)—Q—R substituent, R₁ on ring.

| Compound No. | R₁ | R₂ | R₃ | R₄ | Q | R |
|---|---|---|---|---|---|---|
| 343 | Et | Me | Me | Ph | —CO— | —NH—CH₂CH₂—N(piperazine)N—CH₂Ph—Cl (p) |
| 344 | Et | Me | Me | Ph | —CO— | —NH—CH₂CH₂—N(piperazine)N—CH₂Ph—NO₂ (p) |
| 345 | Et | Me | Me | Ph | —CO— | —NH—CH₂CH₂—N(piperazine)N—CH₂Ph—Cl₂ (2, 4) |
| 346 | Et | Me | Me | Ph | —CO— | —NH—CH₂CH₂—N(piperazine)N—Ph |
| 347 | Et | Me | Me | Ph | —CO— | —NH—CH₂CH₂—N(homopiperazine)N—CH₂Ph—F (p) |
| 348 | Et | Me | Me | Ph | —CO— | —NH—CH₂CH₂—N(homopiperazine)N—CH₂Ph—Cl (p) |
| 376 | —CH₂Ph | Et | Et | H | —CO— | —NH—CH₂CH₂—N(piperazine)N—CH₂P |
| 377 | —CH₂Ph | Et | Et | H | —CO— | —NH—CH₂CH₂—N(piperazine)N—CH₂Ph—F (p) |
| 379 | " | Et | Et | H | —CO— | —NH—CH₂CH₂—N(piperazine)N—CH₂Ph—Cl (p) |
| 381 | " | Et | Et | H | —CO— | —NH—CH₂CH₂—N(piperazine)N—CH₂Ph—Cl (o) |
| 382 | " | Et | Et | H | —CO— | —NH—CH₂CH₂—N(homopiperazine)N—CH₂Ph—Cl (p) |
| 491 | Et | Me | Me | H | —CH₂— | —N(morpholine)O |
| 492 | Et | Me | Me | H | —CH₂— | —N(piperidine)CH₂ |
| 493 | Et | Me | Me | H | —CH₂— | —N(ring)CH—Me |

TABLE 1-continued

Structure: pyrazine ring with R3, R2 substituents, and O—CH(R4)—Q—R side chain; R1 on ring.

| Compound No. | R₁ | R₂ | R₃ | R₄ | Q | R |
|---|---|---|---|---|---|---|
| 494 | Et | Me | Me | H | —CH₂— | —N(piperazine)N—Me |
| 495 | Et | Me | Me | H | —CH₂— | —N(piperazine)N—CH₂CH₂—OH |
| 496 | Et | Me | Me | H | —CH₂— | —N(piperazine)N—CH₂CH₂—O—CH₂CH₂—OH |
| 497 | Et | Me | Me | H | —CH₂— | —N(piperazine)N—CH₂Ph |
| 498 | Et | Me | Me | H | —CH₂— | —N(piperazine)N—CH₂Ph—Cl (p) |
| 499 | Et | Me | Me | H | —CH₂— | —N(piperazine)N—CH₂Ph—OMe (p) |
| 500 | Et | Me | Me | H | —CH₂— | —N(piperazine)N—CH₂Ph—F (p) |
| 501 | Et | Me | Me | H | —CH₂— | —N(piperazine)N—CH₂Ph—NO₂ (p) |
| 502 | Et | Me | Me | H | —CH₂— | —N(homopiperazine)N—CH₂Ph—NO₂ (p) |
| 503 | Et | Me | Me | H | —CH₂— | —N(homopiperazine)N—CH₂Ph—F (p) |
| 504 | Et | Me | Me | H | —CH₂— | —N(homopiperazine)N—CH₂Ph—Cl (p) |
| 511 | —CH₂Ph | Me | Me | H | —CH₂— | —N(morpholine)O |
| 512 | " | Me | Me | H | —CH₂— | —N(piperazine)N—CH₂Ph |
| 516 | " | Me | Me | H | —CH₂— | —N(homopiperazine)N—CH₂Ph—Cl (p) |

TABLE 1-continued

Structure: R₃, R₂ substituted pyrazine with O—CH(R₄)—Q—R and R₁ substituents

| Compound No. | R₁ | R₂ | R₃ | R₄ | Q | R |
|---|---|---|---|---|---|---|
| 536 | Me | Me | Me | H | —CH₂— | —N(CH₂CH₂)₂O (morpholine) |
| 537 | Me | Me | Me | H | —CH₂— | —N(CH₂CH₂)₂CH₂ (pyrrolidine) |
| 538 | Me | Me | Me | H | —CH₂— | —N(CH₂CH₂)₂N—CH₂Ph (piperazine) |
| 539 | Me | Me | Me | H | —CH₂— | —N(CH₂CH₂)₂N—CH₂Ph—Cl (p) |
| 540 | Me | Me | Me | H | —CH₂— | —N(CH₂CH₂)₂N—CH₂Ph—F (p) |
| 541 | Me | Me | Me | H | —CH₂— | —N(CH₂CH₂CH₂)₂N—CH₂Ph—Cl (p) |
| 544 | iso-Pro | Me | Me | H | —CH₂— | —N(CH₂CH₂)₂O |
| 546 | " | Me | Me | H | —CH₂— | —N(CH₂CH₂)₂N—CH₂Ph—Cl (p) |
| 547 | " | Me | Me | H | —CH₂— | —N(CH₂CH₂CH₂)₂N—CH₂Ph—Cl (p) |
| 550 | " | Et | Et | H | —CH₂— | —N(CH₂CH₂)₂CH₂ |
| 551 | " | Et | Et | H | —CH₂— | —N(CH₂CH₂)₂N—Bu |
| 552 | iso-Pro | Et | Et | H | —CH₂— | —N(CH₂CH₂)₂N—CH₂Ph |
| 553 | " | Et | Et | H | —CH₂— | —N(CH₂CH₂CH₂)₂N—CH₂Ph—OMe (p) |
| 556 | iso-Bu | Et | Et | H | —CH₂— | —N(CH₂CH₂)₂N—CH₂Ph |

TABLE 1-continued structure with $R_3$, $R_2$ on pyrazine ring, $O-CH(R_4)-Q-R$ substituent, and $R_1$

| Compound No. | R₁ | R₂ | R₃ | R₄ | Q | R |
|---|---|---|---|---|---|---|
| 558 | " | Et | Et | H | —CH₂— | —N⟨piperazine⟩N—CH₂Ph—OMe (p) |
| 648 | Me | Me | Me | H | —CO— | —NH—CH₂CH₂—Br |
| 649 | Me | Me | Me | H | —CO— | —NH—CH₂CH₂—Cl |
| 650 | Me | Me | Me | H | —CO— | —NH—CH₂CH₂—C₆H₁₁ |
| 651 | Et | Me | Me | Ph | —CO— | —OMe |
| 652 | Et | Me | Me | Ph | —CO— | —OH |
| 653 | Et | Me | Me | Ph | —CO— | —NH—CH₂CH₂—Cl |
| 654 | —CH₂Ph | Et | Et | H | —CO— | —OMe |
| 655 | " | Et | Et | H | —CO— | —OH |
| 656 | " | Et | Et | H | —CO— | —NH—CH₂CH₂—Cl |
| 657 | " | Et | Et | H | —CO— | —NH—CH₂CH₂—N⟨morpholine⟩O |
| 658 | " | Et | Et | H | —CO— | —NH—CH₂CH₂—N⟨piperazine⟩N—Ph |
| 662 | Et | Me | Me | H | —CO— | —OMe |
| 663 | —CH₂Ph | Me | Me | H | —CO— | —OMe |
| 664 | iso-Pro | Me | Me | H | —CO— | —OMe |
| 665 | " | Et | Et | H | —CO— | —OMe |
| 666 | iso-Pro | Et | Et | H | —CO— | —OMe |
| 679 | Me | Me | Me | H | —CH₂— | —OH |
| 680 | Et | Me | Me | H | —CH₂— | —OH |
| 681 | —CH₂Ph | Me | Me | H | —CH₂— | —OH |
| 682 | iso-Pro | Me | Me | H | —CH₂— | —OH |
| 683 | " | Et | Et | H | —CH₂— | —OH |
| 684 | iso-Bu | Et | Et | H | —CH₂— | —OH |
| 697 | iso-Pro | Me | Me | H | —CH₂— | —N⟨piperazine⟩N—Bu |
| 810 | Me | Me | Me | H | —CH₂— | —N⟨piperazine⟩N—Bu |
| 812 | Et | Me | Me | H | —CH₂— | —N⟨piperazine⟩N—Bu |
| 814 | iso-Pro | Me | Me | H | —CH₂— | —N⟨piperazine⟩N—Bu |
| 822 | Me | Me | Me | H | —CH₂— | —N⟨piperazine⟩N—CH₂CH₂—OH |
| 825 | iso-Pro | Me | Me | H | —CH₂— | —N⟨piperazine⟩N—CH₂CH₂—OH |
| 826 | iso-Pro | Et | Et | H | —CH₂— | —N⟨piperazine⟩N—CH₂CH₂—OH |

TABLE 1-continued

| Compound No. | R₁ | R₂ | R₃ | R₄ | Q | R |
|---|---|---|---|---|---|---|
| 834 | iso-Pro | Me | Me | H | —CH₂— | 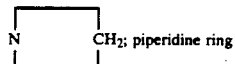 |
| 842 | Me | Me | Me | H | —CH₂— | —NEt₂ |
| 844 | Et | Me | Me | H | —CH₂— | —NEt₂ |
| 846 | iso-Pro | Me | Me | H | —CH₂— | —NEt₂ |
| 848 | iso-Pro | Et | Et | H | —CH₂— | —NEt₂ |

Me; methyl
Et; ethyl
Pro; propyl
Bu; butyl
Ph; benzene ring
( ): position of substituent

 ; piperidine ring

 ; morpholine ring

 ; piperazine ring

 ; homopiperazine ring

TABLE 2

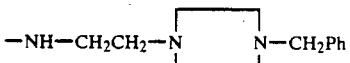

| Compound No. | R₁ | Q | R |
|---|---|---|---|
| 368 | —CH₂Ph | —CO— | —NH—CH₂CH₂—N☐N—CH₂Ph |
| 369 | " | —CO— | —NH—CH₂CH₂—N☐N—CH₂Ph—OMe (p) |
| 370 | " | —CO— | —NH—CH₂CH₂—N☐N—CH₂Ph—Cl (p) |
| 371 | " | —CO— | —NH—CH₂CH₂—N☐N—Ph—Cl (p) |
| 372 | " | —CO— | —NH—CH₂CH₂—N☐N—CH₂Ph—F (p) |
| 373 | " | —CO— | —NH—CH₂CH₂—N☐N—Ph |

TABLE 2-continued

Structure: tetrahydroquinoxaline with 2-O-CH$_2$-Q-R and 3-R$_1$ substituents

| Compound No. | R$_1$ | Q | R |
|---|---|---|---|
| 517 | Bu | —CH$_2$— | morpholino (—N⟨O⟩) |
| 518 | Bu | —CH$_2$— | piperazinyl-N—CH$_2$Ph |
| 519 | Bu | —CH$_2$— | piperazinyl-N—CH$_2$Ph—Cl (p) |
| 520 | Bu | —CH$_2$— | homopiperazinyl-N—CH$_2$Ph—Cl (p) |
| 521 | Bu | —CH$_2$— | piperazinyl-N—Ph |
| 522 | Bu | —CH$_2$— | piperazinyl-N—Ph—OMe (o) |
| 559 | —(CH$_2$)$_4$CH$_3$ | —CH$_2$— | morpholino (—N⟨O⟩) |
| 560 | —(CH$_2$)$_4$CH$_3$ | —CH$_2$— | piperazinyl-N—Bu |
| 561 | " | —CH$_2$— | piperazinyl-N—CH$_2$Ph |
| 562 | " | —CH$_2$— | homopiperazinyl-N—CH$_2$Ph—F (p) |
| 563 | " | —CH$_2$— | piperazinyl-N—Ph—OMe (o) |
| 564 | —(CH$_2$)$_5$CH$_3$ | —CH$_2$— | morpholino (—N⟨O⟩) |
| 565 | " | —CH$_2$— | piperazinyl-N—Bu |
| 567 | " | —CH$_2$— | piperazinyl-N—CH$_2$Ph |
| 568 | " | —CH$_2$— | piperazinyl-N—CH$_2$Ph—Cl (p) |

TABLE 2-continued

Structure: tetrahydroquinoxaline with 2-O-CH₂-Q-R and 3-R₁ substituents

| Compound No. | R₁ | Q | R |
|---|---|---|---|
| 569 | " | —CH₂— | piperazinyl-CH₂Ph—F (p) |
| 570 | " | —CH₂— | piperazinyl-Ph—OMe (o) |
| 571 | —(CH₂)₆CH₃ | —CH₂— | piperazinyl-Bu |
| 572 | —(CH₂)₇CH₃ | —CH₂— | morpholinyl |
| 573 | " | —CH₂— | piperazinyl-Bu |
| 574 | " | —CH₂— | piperazinyl-CH₂Ph |
| 575 | " | —CH₂— | piperazinyl-CH₂Ph—Cl (p) |
| 576 | " | —CH₂— | piperazinyl-CH₂Ph—F (p) |
| 577 | —(CH₂)₇CH₃ | —CH₂— | piperazinyl-Ph |
| 578 | " | —CH₂— | piperazinyl-Ph—OMe (p) |
| 579 | —(CH₂)₈CH₃ | —CH₂— | morpholinyl |
| 580 | " | —CH₂— | piperazinyl-Bu |
| 581 | " | —CH₂— | piperazinyl-CH₂Ph |
| 582 | " | —CH₂— | piperazinyl-CH₂Ph—OMe (p) |

TABLE 2-continued

Structure: tetrahydroquinoxaline with O—CH₂—Q—R at position 2 and R₁ at position 3.

| Compound No. | R₁ | Q | R |
|---|---|---|---|
| 583 | " | —CH₂— | -N(CH₂CH₂CH₂)N—CH₂Ph—Cl (p) |
| 584 | " | —CH₂— | -N(piperazine)N—Ph—Cl (p) |
| 585 | —(CH₂)₉CH₃ | —CH₂— | -N(morpholine)O |
| 586 | " | —CH₂— | -N(piperidine)CH₂ |
| 587 | " | —CH₂— | -N(piperazine)N—Bu |
| 588 | " | —CH₂— | -N(piperazine)N—CH₂CH₂—OH |
| 589 | " | —CH₂— | -N(piperazine)N—CH₂Ph |
| 590 | " | —CH₂— | -N(piperazine)N—CH₂Ph—Cl (p) |
| 591 | " | —CH₂— | -N(piperazine)N—CHPh₂ |
| 592 | " | —CH₂— | -N(CH₂CH₂CH₂)N—CH₂Ph—F (p) |
| 593 | —(CH₂)₉CH₃ | —CH₂— | -N(piperazine)N—Ph—OMe (p) |
| 594 | —(CH₂)₁₁CH₃ | —CH₂— | -N(morpholine)O |
| 595 | " | —CH₂— | -N(piperazine)N—Bu |
| 596 | " | —CH₂— | -N(piperazine)N—CH₂Ph |
| 597 | " | —CH₂— | -N(piperazine)N—CH₂Ph—OMe (p) |

TABLE 2-continued
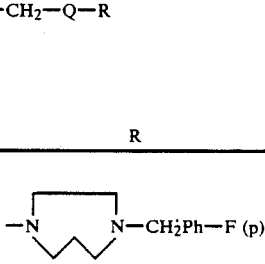
| Compound No. | R₁ | Q | R |
|---|---|---|---|
| 598 | " | —CH₂— | 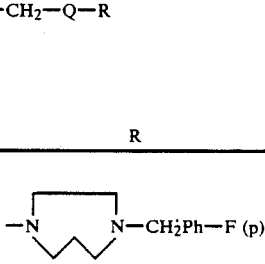 |
| 599 | " | —CH₂— | 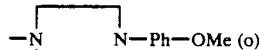 |
| 600 | —(CH₂)₁₃CH₃ | —CH₂— | 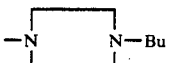 |
| 601 | " | —CH₂— | 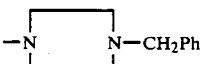 |
| 602 | " | —CH₂— | 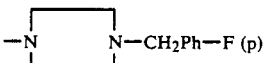 |
| 603 | " | —CH₂— | 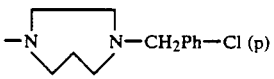 |
| 604 | " | —CH₂— | 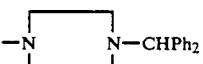 |
| 605 | " | —CH₂— | 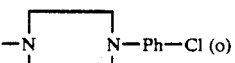 |
| 606 | —(CH₂)₁₅CH₃ | —CH₂— | 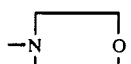 |
| 607 | " | —CH₂— | 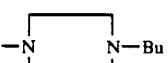 |
| 608 | " | —CH₂— | 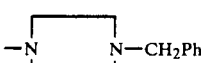 |
| 609 | —(CH₂)₁₅CH₃ | —CH₂— | 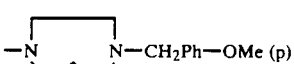 |
| 610 | " | —CH₂— | 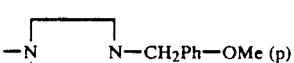 |
| 659 | —CH₂Ph | —CO— | —OMe |
| 660 | " | —CO— | —OH |
| 661 | " | —CO— | —NH—CH₂CH₂—Cl |
| 667 | Bu | —CO— | —OMe |
| 668 | —(CH₂)₄CH₃ | —CO— | —OMe |
| 669 | —(CH₂)₅CH₃ | —CO— | —OMe |
| 670 | —(CH₂)₆CH₃ | —CO— | —OMe |
| 671 | —(CH₂)₇CH₃ | —CO— | —OMe |

TABLE 2-continued structure: tetrahydroquinoxaline with N=C(O—CH₂—Q—R) and N=C(R₁)

| Compound No. | $R_1$ | Q | R |
|---|---|---|---|
| 672 | $-(CH_2)_8CH_3$ | $-CO-$ | $-OMe$ |
| 673 | $-(CH_2)_9CH_3$ | $-CO-$ | $-OMe$ |
| 674 | $-(CH_2)_{11}CH_3$ | $-CO-$ | $-OMe$ |
| 675 | $-(CH_2)_{13}CH_3$ | $-CO-$ | $-OMe$ |
| 676 | $-(CH_2)_{15}CH_3$ | $-CO-$ | $-OMe$ |
| 677 | Pro | $-CO-$ | $-OMe$ |
| 678 | sec-Bu | $-CO-$ | $-OMe$ |
| 685 | Bu | $-CH_2-$ | $-OH$ |
| 686 | $-(CH_2)_4CH_3$ | $-CH_2-$ | $-OH$ |
| 687 | $-(CH_2)_5CH_3$ | $-CH_2-$ | $-OH$ |
| 688 | $-(CH_2)_6CH_3$ | $-CH_2-$ | $-OH$ |
| 689 | $-(CH_2)_7CH_3$ | $-CH_2-$ | $-OH$ |
| 690 | $-(CH_2)_8CH_3$ | $-CH_2-$ | $-OH$ |
| 691 | $-(CH_2)_9CH_3$ | $-CH_2-$ | $-OH$ |
| 692 | $-(CH_2)_{11}CH_3$ | $-CH_2-$ | $-OH$ |
| 693 | $-(CH_2)_{13}CH_3$ | $-CH_2-$ | $-OH$ |
| 694 | $-(CH_2)_{15}CH_3$ | $-CH_2-$ | $-OH$ |
| 695 | Pro | $-CH_2-$ | $-OH$ |
| 696 | sec-Bu | $-CH_2-$ | $-OH$ |
| 817 | Bu | $-CH_2-$ | $-N\underset{\phantom{.}}{\boxed{\phantom{xx}}}N-Bu$ (piperazine) |
| 830 | $-(CH_2)_7CH_3$ | $-CH_2-$ | $-N\underset{\phantom{.}}{\boxed{\phantom{xx}}}N-CH_2CH_2-OH$ (piperazine) |
| 837 | Bu | $-CH_2-$ | $-N\underset{\phantom{.}}{\boxed{\phantom{xx}}}CH_2$ (piperidine) |
| 839 | $-(CH_2)_7CH_3$ | $-CH_2-$ | $-N\underset{\phantom{.}}{\boxed{\phantom{xx}}}CH_2$ (piperidine) |
| 850 | Bu | $-CH_2-$ | $-NEt_2$ |
| 851 | $-(CH_2)_7CH_3$ | $-CH_2-$ | $-NEt_2$ |

Me; methyl
Et; ethyl
Pro; propyl
Bu; butyl
Ph; benzene ring
( ): position of substituent

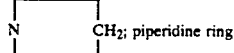
N⎍CH₂; piperidine ring

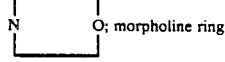
N⎍O; morpholine ring

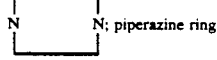
N⎍N; piperazine ring

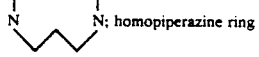
N⎍N; homopiperazine ring

The pharmacological activity of the present compounds [1] is illustrated below All the compounds [1] used in the pharmacological tests were tested in the form of the hydrochloride salt thereof.

1. Platelet aggregation inhibition

Sample solution containing a compound [1] (final concentration 500 or 100 μM) is added to rabbit platelet plasma to which was added 10% by volume of a 3.8% sodium citrate solution, and the mixture is incubated at 37° C. for 3 minutes. A platelet activation factor (PAF, final concentration 10–50 μg/ml) or collagen (final concentration 2.5 μg/ml) is added thereto as an aggregating agent, and platelet aggregation activity is measured with an aggregometer. The results of assays for PAF-induced aggregation are shown in Table 3, and those for collagen-induced aggregation are shown in Table 4, which tables show the strong platelet aggregation inhibitory activity of the compounds [1] of the present invention.

TABLE 3

Platelet aggregation inhibitory action on PAF-induced aggregation

| Compound No. | concentration (μM) | inhibition ratio (%) |
|---|---|---|
| 560 | 100 | 97 |
| 561 | 100 | 56 |
| 562 | 100 | 45 |
| 565 | 100 | 94 |
| 567 | 100 | 58 |
| 570 | 100 | 40 |
| 571 | 100 | 88 |
| 573 | 100 | 86 |
| 580 | 100 | 94 |
| 587 | 100 | 91 |
| 588 | 100 | 64 |
| 595 | 100 | 85 |
| 600 | 100 | 52 |
| 067 | 300 | 53 |
| 070 | 500 | 48 |
| 135 | 500 | 77 |
| 136 | 100 | 50 |
| 137 | 100 | 76 |
| 341 | 100 | 42 |
| 342 | 100 | 43 |
| 344 | 100 | 44 |
| 347 | 100 | 59 |
| 348 | 100 | 70 |
| 502 | 100 | 81 |
| 503 | 100 | 42 |
| 504 | 100 | 60 |
| 541 | 100 | 44 |
| 550 | 100 | 56 |
| 551 | 100 | 97 |
| 552 | 100 | 78 |
| 553 | 100 | 82 |
| 556 | 100 | 51 |

TABLE 4

Platelet aggregation inhibitory action on collagen-induced aggregation

| compound No. | concentration (μM) | inhibition ratio (%) |
|---|---|---|
| 573 | 100 | 58 |
| 580 | 100 | 80 |
| 582 | 100 | 58 |
| 585 | 100 | 41 |
| 587 | 100 | 79 |
| 588 | 100 | 78 |
| 547 | 100 | 56 |
| 550 | 100 | 85 |
| 556 | 100 | 40 |

2. Vasodilation activity

A dog, pretreated with morphine (1.5 mg/kg, sc) is anesthesized with urethane (450 mg/kg, iv) and α-chloralose (45 mg/kg, iv), and immobilized in the dosal position. Right femoral arterial blood is introduced into a left femoral artery via a perfusion pump, and Sterling's resistance is connected to the exosomatic circulatory system to perfuse blood to a left back limb at constant pressure. The perfusion pressure is set at a valve slightly higher than that of the average blood pressure of the animal. Sample (100 μg) dissolved in physiological saline solution is administered to a right femoral artery, and changes in blood flow are measured. Vasodilation activity is measured as a relative activity, by defining as 100% the increased rate of blood flow when 30 μg papaverin is administered intraarterially. The results are shown in Table 5, where it will be seen that the compounds [1] of the present invention have strong vasodilation activity.

TABLE 5

| compound No. | vasodilation activity (%) |
|---|---|
| 075 | 89 |
| 135 | 242 |
| 136 | 204 |
| 137 | 216 |

3. Antioxidant activity

Antioxidant activity is determined according to the method of Stocks et al. [*Clin. Sci. Mol. Med.*, 47: 215 (1974)]. Rat cerebrum is added to ice-cooled 40 mM phosphate saline buffer solution (PBS) (pH 7.4, 4 ml buffer per 1 g cerebrum), homogenized and centrifuged (1000×g, 4° C., 10 min.) to obtain a supernatant solution. The supernatant solution is diluted fivefold with the above ice-cooled PBS solution, and to a 0.9 ml aliquot thereof is added a sample containing a compound [1] (0.1 ml, final concentration 100 μM) dissolved in ethanol. The resultant mixture is incubated at 37° C. for 15 minutes, 35% perchloric acid (0.2 ml) is added, and the mixture is ice-cooled to stop the reaction and centrifuged (1300×g, 4° C., 10 min.). 0.5 ml thiobarbituric acid (5 g/lit. of 50% acetic acid) is added to the supernatant solution (1 ml), so as to measure its absorbancy at 532 nm. The amount of lipoperoxide thus generated is expressed as an amount of malondialdehyde. The results are shown in Table 6, where it will be seen that the compounds [1] of the present invention inhibit lipoperoxide generation.

TABLE 6

| compound No. | inhibition ratio (%) |
|---|---|
| 371 | 49 |
| 372 | 64 |
| 373 | 49 |
| 520 | 83 |
| 562 | 65 |
| 568 | 61 |
| 569 | 81 |
| 570 | 65 |
| 573 | 56 |
| 574 | 71 |
| 575 | 79 |
| 576 | 85 |
| 577 | 71 |
| 578 | 88 |
| 580 | 77 |
| 581 | 71 |
| 582 | 82 |
| 583 | 82 |
| 584 | 65 |
| 585 | 62 |
| 586 | 68 |
| 587 | 65 |
| 588 | 65 |
| 589 | 74 |
| 590 | 74 |
| 591 | 59 |
| 592 | 85 |
| 593 | 73 |
| 594 | 58 |
| 595 | 70 |
| 596 | 73 |
| 597 | 76 |
| 598 | 88 |
| 599 | 70 |
| 600 | 61 |
| 601 | 67 |

TABLE 6-continued

| Antioxidant activity | |
|---|---|
| compound No. | inhibition ratio (%) |
| 602 | 64 |
| 603 | 76 |
| 607 | 52 |
| 608 | 55 |
| 609 | 61 |
| 344 | 48 |
| 345 | 54 |
| 347 | 51 |
| 348 | 62 |
| 379 | 50 |
| 382 | 83 |
| 502 | 69 |
| 516 | 75 |

As explained hereinabove, a compound [1] of the present invention or its corresponding salt inhibits platelet aggregation, has-vasodilating activity, and/or inhibits lipoperoxide generation, and is useful in pharmaceutical form for treating circulatory and metabolic disorders.

The following examples are illustrative of the present invention but are not to be construed as limiting.

In the examples, the Rf value of silica-gel thin layer chromatography (TLC) is either specified by or measured using the following carrier and developing solvent:

Carrier: silica gel, Kieselgel 60 $F_{254}$ Art 5715 (Merck)
Developer: chloroform - methanol (20:1)

Physical properties (NMR, Mass, CI, Rf upon TLC) of the compounds [1] obtained in the following examples are shown in Tables 25–27.

Symbols for chemical structure in Tables 7–19 have the same meanings as in Table 1, and the symbols in Tables 20–24 have the same meanings as in Table 2.

EXAMPLE 1

Methyl (3,5,6-trimethylpyrazine-2-yl oxy) acetate (compound 034)

Metallic sodium (1.29 g, 56 mM) was dissolved in anhydrous methanol (120 ml). 2-hydroxy-3,5,6-trimethylpyrazine (7.74 g, 56 mM) was dissolved therein, and methanol was distilled off in vacuo to obtain sodium 3,5,6-trimethyl-2-pyrazinolate which was suspended in dimethylformamide (150 ml). Methyl chloroacetate (10.85 g, 0.10M) was added thereto and the mixture was stirred at 95°-100° C. for 3 hours. The solvent was removed in vacuo. Dilute aqueous sodium carbonate was added to the residue, which was then extracted twice with chloroform (200 ml), and the extract was dried with anhydrous magnesium sulfate and concentrated in vacuo. The residue was charged on a column of silica gel (Wako Pure Chem. Co., C-200, 170 g) and eluted with benzene and benzene-ethyl acetate (10:1) successively to obtain the product. (8.23 g, yield: 70.0%)

EXAMPLE 2

Methyl α-(3,5,6-trimethylpyrazine-2-yl oxy) propionate (compound 035)

Methyl α-chloropropionate (12.25 g, 0.10 mM) was added to sodium 3,5,6-trimethyl-2-pyrazinolate (8.00 g, 50 mM) suspended in dimethylformamide (100 ml) and the mixture was stirred 95°-100° C. for 7 hours. The solvent was distilled off in vacuo. Dilute aqueous sodium carbonate was added to the residue, which was then extracted once with chloroform (200 ml) and twice with chloroform (100 ml), and the extract was dried with anhydrous magnesium sulfate and concentrated in vacuo. The residue was charged on a column of silica gel (Wako Pure Chem. Co., C-200, 160 g) and eluted wtih benzene and benzene-ethyl acetate (10:1) successively to obtain the product. (8.39 g, yield: 74.9%)

EXAMPLE 3

Methyl α-(3,5,6-trimethylpyrazine-2-yl oxy) phenyl acetate (compound 036)

Methyl α-bromophenyl acetate (23.0 g, 0.10 mM) was added to sodium 3,5,6-trimethyl-2-pyrazinolate (8.00 g, 50 mM) suspended in dimethylformamide (150 ml) and the mixture was stirred at 100° C. for 5 hours. The reaction mixture was treated in the same way as in Example 2 to obtain the product. (10.97 g, yield: 76.7%)

EXAMPLE 4

(3,5,6-trimethylpyrazine-2-yl oxy) acetate (compound 037)

Aqueous 1N-NaOH (80 ml) was added to compound 034 (8.40 g, 40 mM) and the mixture was stirred for 30 minutes. 1N-HCl (80 ml) was added to the reaction mixture and the precipitated crystals were collected by filtration to obtain a portion of the product. (3.15 g) The filtrate was dried in vacuo and the residue was extracted with hot ethanol, then the extract was dried in vacuo to obtain the remainder of the product. (4.09 g) (Total: 7.24 g, yield: 92.3%)

EXAMPLE 5

α-(3,5,6-trimethylpyrazine-2-yl oxy) propionate (compound 038)

Aqueous 1N-NaOH (80 ml) was added to compound 035 (7.81 g, 35 mM) and the mixture was stirred for 1 hour. The reaction mixture was extracted with chloroform to remove unreacted compound. 1N-HCl (70 ml) was added to the aqueous layer and the mixture was concentrated in vacuo to precipitate crystals, which were collected by filtration, washed with water completely and dried to obtain the product. (6.66 g, yield: 90.6%)

EXAMPLE 6

α-(3,5,6-trimethylpyrazine-2-yl oxy) phenyl acetate (compound 039)

Aqueous 1N-NaOH (75 ml) was added to compound 0.36 (10.80 g, 37.7 mM) dissolved in methanol (75 ml) and the mixture was stirred for 1.5 hour. Methanol was distilled off in vacuo and the aqueous layer was washed with chloroform. 1N-HCl (75 ml) was added to the aqueous layer which was extracted with chloroform. The extract was dried with anhydrous magnesium sulfate and concentrated in vacuo to obtain the product as white crystals. (9.89 g, yield: 96.4%

EXAMPLES 7-12

2-(substituted carbonylmethoxy)-3,5,6-trimethylpyrazine

Triethylamine (0.70 ml, 5 mM) was added to compound 037 (0.98 g, 5 mM) dissolved in tetrahydrofuran Pivaloyl chloride (0.16 g, 5 mM) was added dropwise at −5° C. and the mixture was stirred for 30 minutes with ice cooling. A tetrahydrofuran solution of a base (5 mM) was added dropwise to the reaction mixture and the mixture was stirred at room temperature for 4 hours. The reaction mixture was concentrated in vacuo and the residue was dried with chloroform, then concentrated in vacuo. The residue was charged on a column of silica gel (C-20, 60 g) and eluted with chloroform and chloroform-methanol (200:1) successively to obtain the compounds in Table 7.

Table 7 identifies the product, yields in weight and percentage, the base and its amount used.

EXAMPLE 13

N-(2-bromoethyl)-3,5,6-trimethylpyrazine-2-yl oxy) acetamide (compound 648)

Triethylamine (7.0 ml, 50 mM) was added to compound 037 (9.80 g, 50 mM) dissolved in tetrahydrofuran (100 ml) and chloroform (100 ml) in solution with bromoethylamine hydrobromide (10.30 g, 50 mM) and triethylamine (7.7 ml, 55 mM) was added dropwise at −5° C., then the mixture was stirred for 4 hours with ice cooling. The reaction mixture was concentrated in vacuo, the residue was dissolved in chloroform and washed with dilute aqueous potassium carbonate. The aqueous layer was extracted with chloroform. The organic layer was combined, dried with anhydrous magnesium sulfate, and concentrated in vacuo. The residue was charged on a column of silica gel (Chlodil, 250 g), and eluted successively with chloroform and chloroform-methanol (500:1) to obtain the product (6.92 g)

EXAMPLE 14

N-(2-chloroethyl)-(3,5,6-trimethylpyrazine-2-yl oxy) acetamide (compound 649)

Triethylamine (3.50 ml, 25 mM) was added to compound 037 (4.90 g, 25 mM) dissolved in tetrahydrofuran (50 ml) and pivaloyl chloride (3.05 g, 25 mM) was added dropwise at −5° C., then the mixture was stirred for 30 mintes. Chloroform (50 ml) in solution with 2-chloroethylamine hydrochloride (2.90 g, 25 mM) and triethylamine (3.9 ml, 28 mM) was added dropwise thereto, then the mixture was stirred for 4 hours while slowly reaching room temperature. The reaction mixture was concentrated in vacuo, the residue was dissolved in chloroform and washed with dilute aqueous potassium carbonate. The aqueous layer was extracted with chloroform. The organic layer was combined, dried with anhydrous magnesium sulfate, and concentrated in vacuo. The residue was charged on a column of silica gel (C-200, 40 g), and eluted successively with chloroform and chloroform-methanol (20:1) to obtain the product (5.66 g, yield: 7.5%)

EXAMPLES 15-21

N-(2-substituted ethyl)-(3,5,6-trimethylpyrazine-2-yl oxy) acetamide:

Benzene (20 ml) in solution with compound 648 (0.91 g, 3.0 mM), triethylamine (0.84 ml) and a base was refluxed. The reaction mixture was washed with dilute aqueous potassium carbonate, and the aqueous layer was extracted with chloroform. The organic layers (benzene and chloroform) was combined, dried with anhydrous magnesium sulfate, and concentrated in vacuo. The residue was charged on a column of silica gel (C-200, 65 g) and eluted successively with chloroform and chloroform-methanol to obtain the compounds in Table 8.

Table 8 shows the reflux time, yield in weight and percentage, the base and its amount used and the ratio of chloroform-methanol mixture used in each of the above examples.

EXAMPLE 22

N-(2-phenylthioethyl)-(3,5,6-trimethylpyrazine-2-yl oxy) acetamide (compound 072)

Thiophenol (0.60 g, 5.4 mM) and potassium carbonate (0.75 g, 5.4 mM) were added to compound 648 (0.91 g, 3.0 mM) dissolved in dimethylformamide (10 ml) and the mixture was stirred for 2 hours at room temperature. The reaction mixture was concentrated in vacuo, the residue was dissolved in chloroform and washed with dilute aqueous potassium carbonate. The aqueous layer was further extracted with chloroform. The combined organic layer was chromatographed by eluting successively with benzene and benzene-ethyl acetate (10:1) to obtain the product (0.35 g, yield: 35.2%)

EXAMPLES 23-25

N-(2-substituted ethyl)-(3,5,6-trimethylpyrazine-2-yl oxy) acetamide

Benzene (25 ml) in solution with compound 649 (0.98 g, 4 mM), triethylamine (1.14 ml) and a base was refluxed. The reaction mixture was washed with dilute aqueous potassium carbonate, and the aqueous layer was further extracted with chloroform. The organic layers (benzene and chloroform) were combined, dried with anhydrous magnesium sulfate, and concentrated in vacuo. The residue was charged on a column of silica gel (C-200, 80 g) and eluted successively with chloroform and chloroform-methanol to obtain the compounds in Table 9.

Table 9 shows the identity of the base and its amount used, the reflux time, the ratio of chloroform-methanol mixture used, the products and the yield in weight and percentage, in each of the above examples.

EXAMPLE 26

Methyl α-(3-ethyl-5,6-dimethylpyrazine-2-yl oxy) phenyl acetate (compound 651)

A solution (12.5 ml) of 4N-CH$_3$ONa/methanol was added to a solution of 2-hydroxy-3-ethyl-5,6-dimenthyl-pyrazine (7.60 g, 50 mM) in anhydrous methanol (100 ml), and methanol was distilled off in vacuo. The residue was dissolved in dimethylformamide (150 ml).

Methyl α-bromophenyl acetate (11.5 g, 50 mM) was added thereto, and the mixture was stirred at 100° C. for 5 hours. The reaction mixture was concentrated in vacuo. The residue was dissolved in chloroform, and washed with dilute aqueous potassium carbonate. The aqueous layer was further extracted twice with chloroform. The organic layers were combined, dried with anhydrous magnesium sulfate, and concentrated in vacuo. The residue was charged on a column of silica gel (C-200, 170 g) and eluted successively with benzene and benzene-ethyl acetate (50:1) to obtain the product (10.42 g, yield 69.5%)

EXAMPLE 27

α-(3-ethyl-5,6-dimethylpyrazine-2-yl oxy) phenyl acetate (compound 652):

Aqueous 2N-NaOH (25.7 ml) was added to compound 651 (7.72 g, 25.7 mM) dissolved in methanol (30 ml) and the mixture was stirred for 4.5 hours at room temperature. The reaction mixture, to which 2N-HCl (25.7 ml) was added, was ice cooled to precipitate crystals. The thus-precipitated crystals were collected by filtration, washed with water and dried to obtain the product (6.91 g, yield: 94.0%)

EXAMPLE 28

N-(2-chloroethyl)-α-(3-ethyl-5,6-dimethylpyrazine-2-yl oxy) phenyl acetamide (compound 653)

Triethylamine (3.7 ml, 26.6 mM) was added to compound 652 (7.50 g, 26.2 mM) dissolved in tetrahydrofuran (44 ml) and pivaloylchloride (3.21 g, 26.3 mM) was added dropwise at −5° C., then the mixture was stirred for 30 minutes. Chloroform (26 ml) in solution with 2-chloroethylamine hydrochloride (3.05 g, 26.3 mM) and triethylamine (3.7 ml) was added dropwise thereto with cooling at 0°–5° C., then the mixture was stirred for 1 hour with ice cooling and for 4 hours at room temperature. Chloroform was added to the reaction mixture and the mixture was washed with dilute aqueous potassium carbonate. The aqueous layer was further extracted twice with chloroform. The organic layer were combined, dried with anhydrous magnesium sulfate, and concentrated in vacuo. The residue was charged on a column of silica gel (C-200, 170 g), and eluted successively with benzene, benzene-ethyl acetate (40:1) and benzene-ethyl acetate (10:1) to obtain the product (6.46 g, yield 70.4%)

EXAMPLES 29–36

N-(2-substituted ethyl)-α-(3-ethyl-5,6-dimethylpyrazine-2-yl oxy) phenyl acetamide A base (8.0 mM) was added to benzene (30 ml) in solution with compound 653 (1.39 g, 4.0 mM) and triethylamine (1.12 ml) and the mixture was refluxed overnight. The reaction mixture was washed with dilute aqueous potassium carbonate, and the aqueous layer was further extracted three times with chloroform. The organic layers (benzene and chloroform) were combined, dried with anhydrous magnesium sulfate, and concentrated in vacuo. The residue was charged on a column of silica gel (C-200, 65 g) and eluted successively with chloroform and chloroform-methanol (100:1) to obtain the compounds in Table 10.

Table 10 shows the identity of the base and its amount used, the compounds and their yield in weight and percentage in each of the above examples.

EXAMPLE 37

Methyl (3-benzyl-5,6-diethylpyrazine-2-yl oxy) acetate (compound 654)

A solution of 4N-CH$_3$ONa/methanol (10.0 ml, 40 mM) was added to a solution of 2-hydroxy-3-benzyl-5,6-diethylpyrazine (9.68 g, 40 mM) in anhydrous methanol (120 ml), and methanol was distilled off in vacuo. The residue was dissolved in dimethylformamide (150 ml). Methyl chloroacetate (4.34 g, 40 mM) was added thereto, and the mixture was stirred at 100° C. for 5 hours. The reaction mixture was concentrated in vacuo, diluted aqueous potassium carbonate was added to the residue and the aqueous layer was extracted three times with chloroform. The extract was dried with anhydrous magnesium sulfate, and concentrated in vacuo. The residue was charged on a column of silica gel (C-200, 170 g) and eluted successively with benzene and benzene-ethyl acetate (100:1) to obtain the product. (11.41 g, yield: 90.8%)

EXAMPLE 38

(3-benzyl-5,6-diethylpyrazine-2-yl oxy) acetate (compound 655)

Aqueous 2N-NaOH (34 ml) was added to compound 954 (10.68 g, 34.0 mM) dissolved in methanol (34 ml) and the mixture was stirred for 3 hours. 2N-HCl (34 ml) was added to the reaction mixture and the precipitated crystals were collected by filtration, washed completely with water and dried to obtain the product. (8.86 g, yield: 86.9%)

EXAMPLE 39

N-(2-chloroethyl)-(3-benzyl-5,6-diethylpyrazine-2-yl oxy) acetamide (compound 656)

Pivaloyl chloride (3.66 g, 30 mM) was added dropwise at −5° C. to compound 655 (8.62 g, 28.7 mM) and triethylamine (4.2 ml, 30 mM) dissolved in tetrahydrofuran (50 ml), then the mixture was stirred for 30 minutes. Chloroform (30 ml) in solution with 2-fluoroethylamine hydrochloride (3.48 g) and triethylamine (4.2 ml) was added dropwise thereto with cooling at 0° to −5° C. then the mixture was stirred for 1 hour with ice cooling and 4 hours at room temperature. Dilute aqueous potassium carbonate was added to the reaction mixture and the mixture was extracted three times with chloroform. The extract was dried with anhydrous magnesium sulfate, and concentrated in vacuo. The residue was charged on a column of silica gel (C-200, 175 g) and eluted successively with benzene and benzene-ethyl acetate (5:1) to obtain the product. (9.21 g, yield: 88.8%)

EXAMPLES 40–46

N-(2-substituted ethyl)-(3-benzyl-5,6-dimethylpyrazine-2-yl oxy) acetamide

Benzene (30 ml) in solution with compound 656 (1.27 g, 3.5 mM), triethylamine (0.98 ml, 7 mM) and a base (7 mM) was refluxed. Dilute aqueous potassium carbonate was added to the reaction mixture and the mixture was extracted three times with chloroform. The organic layer was dried with anhydrous magnesium sulfate and concentrated in vacuo. The residue was charged on a column of silica gel (C-200, 80 g) and eluted successively with chloroform and chloroform-methanol (100:1) to obtain the compounds in Table 11.

Table 11 shows the identity of the base and its amount used, the reflux time, and the product and yield in weight and percentage in each of the above examples.

EXAMPLES 47-51

Methyl (3,5,6-trialkylpyrazine-2-yl oxy) acetate

Metallic sodium (1.15 g) was dissolved in anhydrous methanol (100 ml). A starting material 2-hydroxy-3,5,6-trialkylpyrazine (50 mM) was dissolved therein, and methanol was distilled off in vacuo to obtain the sodium salt thereof. Dimethylformamide (100 ml) and methyl chloroacetate (5.43 g, 50 mM) were added thereto, then the mixture was extracted three times with chloroform. The extract was dried with anhydrous magnesium sulfate and concentrated in vacuo. The residue was charged on a column of silica gel (C-200) and eluted successively with benzene and benzene-ethyl acetate (20:1) to obtain the compounds in Table 12.

Table 12 shows the identity of the starting compound and its amount used, the reaction time, the amount of silica gel used and the product and yield in weight and percentage in each of the above examples.

EXAMPLES 52-57

2-(2-hydroxyethoxy)-3,5,6-trialkylpyrazine

A starting compound was dissolved in methanol 6-8 equivalents of NaBH4 were added stepwise while refluxing. The reaction mixture was concentrated in vacuo, water was added thereto, then the mixture was extracted three times with chloroform. The extract was dried with anhydrous magnesium sulfate and concentrated in vacuo. The residue was charged on a column of silica gel (C-200) and eluted successively with benzene and benzene-ethyl acetate (10:1) to obtain the compounds in Table 13.

Table 13 shows the identity of the starting compound and its amount used, the amount of NaBH4 used, the reflux time, the amount of silica gel used and the product and yield in weight and percentage in each of the above examples.

EXAMPLES 58-66

2-(2-substituted ethoxy)-3,5,6-trimethylpyrazine

Thionyl chloride (0.56 ml, 1.3 equivalent) was added dropwise with ice cooling to compound 679 (1.10 g, 6.0 mM) dissolved in chloroform and the mixture was stirred at room temperature for 2.5 hours. Dilute aqueous potassium carbonate was added to the reaction mixture and the mixture was extracted three times with chloroform. The extract, which was dried with anhydrous sodium sulfate, was concentrated in vacuo. Benzene (30 ml), triethylamine (1.68 ml, 12 mM) and a base (12 mM) were added to the residue, and the mixture was refluxed. Dilute aqueous potassium carbonate was added to the reaction mixture, and the mixture was extracted three times with chloroform. The extract was dried with anhydrous magnesium sulfate and concentrated in vacuo. The residue was charged on a column of silica gel (C-200, 75 g) and eluted successively with chloroform and chloroform-methanol (200:1) to obtain the compounds in Table 14.

Table 14 shows the identity of the base and its amount used, the reflux time, and the product and yield in weight and percentage in each of the above examples.

EXAMPLES 67-72

2-(2-substituted ethoxy)-3-isopropyl-5,6-diethylpyrazine

Thionyl chloride (0.47 ml, 1.3 equivalent) was added dropwise with ice cooling to compound 683 (1.19 g, 5.0 mM) dissolved in chloroform (5 ml) and the mixture was stirred at room temperature for 4 hours. Dilute aqueous potassium carbonate was added to the reaction mixture and the mixture was extracted three times with chloroform. The extract, which was dried with anhydrous sodium sulfate, was concentrated in vacuo. Benzene (30 ml), triethylamine (1.40 ml, 10 mM) and a base (10 mM) were added to the residue, and the mixture was refluxed. Dilute aqueous potassium carbonate was added to the reaction mixture, and the mixture was extracted three times with chloroform. The extract was dried with anhydrous magnesium sulfate and concentrated in vacuo. The residue was charged on a column of silica gel (C-200, 75 g) and eluted successively with chloroform and chloroform-methanol (200:1) to obtain the compounds in Table 15.

Table 15 shows the identity of the base and its amount used, the reflux time, and the product and yield in weight and percentage in each of the above examples.

EXAMPLES 73-88

2-(2-substituted ethoxy)-3-ethyl-5,6-dimethylpyrazine

Thionyl chloride (0.43 ml, 1.3 equivalent) was added dropwise with ice cooling to compound 680 (0.98 g, 5.0 mM) dissolved in chloroform (5 ml) and the mixture was stirred at room temperature for 3 hours. Dilute aqueous potassium carbonate was added to the reaction mixture and the mixture was extracted three times with chloroform. The extract, which was dried with anhydrous sodium sulfate, was concentrated in vacuo. Benzene (60 ml), triethylamine (1.40 ml, 10 mM) and a base (10 mM) were added to the residue, and the mixture was refluxed. Dilute aqueous potassium carbonate was added to the reaction mixture, and the mixture was extracted three times with chloroform. The extract was dried with anhydrous magnesium sulfate and concentrated in vacuo. The residue was charged on a column of silica gel (C-200 75 g) and eluted successively with chloroform and chloroform-methanol to obtain the compounds in Table 16.

Table 16 shows the identity of the base and its amount used, the reflux time, the ratio of chloroform-methanol in the column chromatography, and the product and yield in weight and percentage in each of the above examples.

EXAMPLES 89-91

2-(2-substituted ethoxy)-3-benzyl-5,6-dimethylpyrazine:

Thionyl chloride (0.36 ml, 1.3 equivalent) was added dropwise with ice cooling to compound 681 (1.04 g, 4.0 mM) dissolved in chloroform (5 ml) and the mixture was stirred at room temperature for 3 hours. Dilute aqueous potassium carbonate was added to the reaction mixture and the mixture was extracted three times with chloroform. The extract, which was dried with anhydrous sodium sulfate, was concentrated in vacuo. Benzene (30 ml), triethylamine (1.40 ml, 10 mM) and a base (8.0 mM) were added to the residue, and the mixture was refluxed. Dilute aqueous potassium carbonate was added to the reaction mixture, and the mixture was extracted three times with chloroform. The extract was dried with anhydrous magnesium sulfate and concentrated in vacuo. The residue was charged on a column of silica gel (C-200, 75 g) and eluted successively with chloroform and chloroform-methanol to obtain the compounds in Table 17.

Table 17 shows the identity of the base and its amount used, the reflux time, ratio of chloroform-methanol in column chromatography, and the product and yield in weight and percentage in each of the above examples.

EXAMPLES 92-98 2-(2-substituted ethoxy)-3-isopropyl-5,6-dimethylpyrazine

Thionyl chloride (0.47 ml, 1.3 equivalent) was added dropwise with ice cooling to compound 682 (1.05 g, 4.0 mM) dissolved in chloroform (5 ml) and the mixture was stirred at room temperature for 3.5 hours. Dilute aqueous potassium carbonate was added to the reaction mixture and the mixture was extracted three times with chloroform. The extract, which was dried with anhydrous sodium sulfate, was concentrated in vacuo. Benzene (30 ml), triethylamine (1.40 ml, 10 mM) and a base (10 mM) were added to the residue, and the mixture was refluxed. Dilute aqueous potassium carbonate was added to the reaction mixture, and the mixture was extracted three times with chloroform. The extract was dried with anhydrous magnesium sulfate and concentrated in vacuo. The residue was charged on a column of silica gel (C-200, 75 g) and eluted successively with chloroform and chloroform-methanol to obtain the compounds in Table 18.

Table 18 shows the identity of the base and its amount used, the reflux time, the ratio of chloroform-methanol in the column chromatography, and the product and yield in weight and percentage in each of the above examples.

EXAMPLES 99-100

2-(2-substituted ethoxy)-3-isobutyl-5,6-diethylpyrazine:

Thionyl chloride (0.47 ml, 1.3 equivalent) was added dropwise with ice cooling to compound 684 (1.26 g, 5.0 mM) dissolved in chloroform (5 ml) and the mixture was stirred at room temperature for 4 hours. Dilute aqueous potassium carbonate was added to the reaction mixture and the mixture was extracted three times with chloroform. The extract, which was dried with anhydrous sodium sulfate, was concentrated in vacuo. Benzene (30 ml), triethylamine (1.40 ml, 10 mM) and a base (10 mM) were added to the residue, and the mixture was refluxed. Dilute aqueous potassium carbonate was added to the reaction mixture, and the mixture was extracted three times with chloroform. The extract was dried with anhydrous magnesium sulfate and concentrated in vacuo. The residue was charged on a column of silica gel (C-200, 75 g) and eluted successively with chloroform and chloroform-methanol to obtain the compounds in Table 19.

Table 19 shows the identity of the base and its amount used, the reflux time, and the product and yield in weight and percentage in each of the above examples.

Comparative Example 1

2-hydroxy-3-benzyl-5,6,7,8-tetrahydroquinoxaline:

A methanol (30 ml) solution of cyclohexane-1,2-dione (13.44 g, 0.12 M) was added to phenylalanineamide hydrochloride (20.05 g, 0.1 M) dissolved in methanol (200 ml) with cooling below $-30°$ C., and aqueous 12.5 N-NaOH (20 ml) was added dropwise thereto. The reaction mixture was 1 stirred at below $-30°$ C. for 30 minutes and was further stirred at room temperature for 3 hours. Conc. hydrochloric acid (25 ml) was added to the reaction mixture, and sodium bicarbonate (15 g) was added after 10 minutes stirring, the solvent then being distilled off in vacuo. The residue, to which was added water, was extracted three times with chloroform, and the extract was dried with anhydrous magnesium sulfate and concentrated in vacuo. The residue was recrystallized from acetone to obtain the product. (19.7 g, yield: 82.1%)

COMPARATIVE EXAMPLE 2

2-hydroxy-3-(2-phenylethyl)-5,6,7,8-tetrahydroquinoxaline:

A methanol (20 ml) solution of cyclohexane-1,2-dione (5.38 g) was added to o-amino-2-phenylacetic acidamide hydrochloride (8.58 g, 40 mM) dissolved in methanol (100 ml) with cooling below -30° C., and aqueous 12.5 N-NaOH was added dropwise thereto. The reaction mixture was stirred at below $-30°$ C. for 30 minutes, and the mixture was stirred at room temperature for 6 hours. Conc. hydrochloric acid (8 ml) was added to the reaction mixture, and sodium bicarbonate (6.0 g) was added after 10 minutes stirring, the solvent then being distilled off in vacuo. The residue, to which was added water, was extracted three times with chloroform, dried with anhydrous magnesium sulfate and concentrated in vacuo. The residue was recrystallized from acetone to obtain the product. (6.79 g, yield: 66.8%)

COMPARATIVE EXAMPLE 3

2-hydroxy-3-methyl-5,6,7,8-tetrahydroquinoxaline:

A methanol (20 ml) solution of cyclohexane-1,2-dione (6.72 9) was added to alanine (4.4 g, 50 mM) dissolved in methanol (100 ml) with cooling below -30° C., and aqueous 12.5 N-NaOH (5 ml) was added dropwise thereto. The reaction mixture was stirred at below -30° C. for 30 minutes, and the mixture was stirred at room temperature for 3 hours. Conc. hydrochloric acid (8 ml) was added to the reaction mixture, and sodium bicarbonate (5 g) was added after 10 minutes stirring, the solvent then being distilled off in vacuo. The residue, to which was added water, was extracted three times with chloroform, dried with anhydrous magnesium sulfate and concentrated in vacuo. The residue was recrystallized from acetone to obtain the product as pale yellowish crystals. (6.50 g, yield: 79.0%)

COMPARTIVE EXAMPLE 4

2-hydroxy-3-ethyl-5,6,7,8-tetrahydroquinoxaline:

A methanol (20 ml) solution of cyclohexane-1,2-dione (6.72 g, 60 mM) was added to a methanol solution (100 ml) of α-aminobutylamide (5.1 g, 50 mM) with cooling below −30° C., and aqueous 12.5 N-NaOH (5 ml) was added dropwise thereto. The reaction mixture was stirred at below −30° C. for 30 mins. and the mixture was stirred at room temperature for 3 hours. Conc. hydrochloric acid (6.25 ml) was added to the reaction mixture and sodium bicarbonate (5 g) was added after 10 minutes stirring, the solvent being distilled off in vacuo. The residue, to which was added water, was extracted three times with chloroform, dried with anhydrous magnesium sulfate and concentrated in vacuo. The residue was recrystallized from acetone to obtain the colorless crystals. (5.30 gm, yield: 60.0%)

COMPARATIVE EXAMPLES 5–18

2-hydroxy-3-alkyl-5,6,7,8-tetrahydroquinoxaline:

Cyclohexane-1,2-dione (6.72 g, 60 mM) was added a 11 at once to amino acidamine hydrochloride (50 mM) dissolved in methanol (100 ml) with cooling below −30° C., and aqueous 12 N-NaOH (5 ml) was added dropwise thereto. The reaction mixture was stirred for 30 minutes with cooling below −30° C., and the mixture was stirred at room temperature for 5 hours. Conc. hydrochloric acid (12.5 ml) was added to the reaction mixture and sodium bicarbonate (7.5 g) was added after 10 minutes, whereafter the solvent was distilled off in vacuo. The residue, to which was added water, was extracted three times with chloroform, dried with anhydrous sodium sulfate and concentrated in vacuo. The residue was recrystallized from acetone to obtain the products shown in Table 20.

Table 20 shows the identity of the acid amide hydrochloride and its amount used and the product and yield in weight and percentage in each of the above comparative examples.

EXAMPLE 101

Methyl (3-benzyl-5,6,7,8-tetrahydroquinoxaline-2-yl oxy) acetate (compound 656):

2-hydroxy-3-benzyl-5,6,7,8-tetrahydroquinoxaline (12.0 g, 50 mM) was dissolved in a solution of metallic sodium (1.15 g, 50 mM) in anhydrous methanol (200 ml), whereafter methanol was distilled off in vacuo to obtain the sodium salt thereof, which was suspended in dimethylformamide (100 ml). Methyl chloroacetate (5.43 g, 50 mM) was added thereto and the mixture was stirred at 100° C. for 3 hours. The reaction mixture was concentrated in vacuo. Dilute aqueous sodium carbonate was added to the residue, which was then extracted three times with chloroform, and the extract was dried with anhydrous sodium sulfate and concentrated in vacuo. The residue was charge on a column of silica gel (C-200, 180 g) and eluted successively with benzene and benzene-ethyl acetate (10:1) to obtain the product. (14.12 g, yield: 90.5%)

EXAMPLE 102

(3-benzyl-5,6,7,8-tetrahydroquinoxaline-2-yl oxy) acetate (compound 660):

Aqueous 2N-NaOH (30 ml) was added to compound 656 (9.42 g, 30.2 mM) dissolved in methanol (30 ml) and the mixture was stirred for 3 hours at room temperature. 2N-HCl (30 ml) was added to the reaction on mixture with ice cooling and the precipitated crystals were collected by filtration, washed with water and dried to obtain most of the product. (8.10 g) The filtrate was concentrated in vacuo and the residue was extracted with hot ethanol, then the extract was concentrated in vacuo. The residue dissolved in dilute aqueous NaOH, was neutralized with 1 N-HCl and the precipitated crystals were collected by filtration, washed with water, then dried to obtain the remainder of the product. (0.32 g) (Total: 8.42 g, yield: 93.6%)

EXAMPLE 103

N-(2-chloroethyl)-(3-benzyl-5,6,7,8-tetrahydroquinoxaline-2-yl oxy) acetamide (compound 661):

Pivaloyl chloride (3.05 g, 25 mM) was added dropwise at −5° C. to compound 660 (7.45 g, 25 mM) and triethylamine (3.5 ml, 25 mM) dissolved in tetrahydrofuran (45 ml), then the mixture was stirred for 30 minutes. Chloroform (25 ml) in solution with 2-chloroethylamine hydrochloride (2.90 g) and triethylamine (3.5 ml) was added dropwise thereto, then the mixture was stirred for 1 hour with ice cooling and 4 hours at room temperature. Dilute aqueous potassium carbonate was added to the reaction mixture and the mixture was extracted twice with chloroform. The extract was dried with anhydrous sodium sulfate, and concentrated in vacuo. The residue was charged on a column of silica gel (C-200, 175 g) and eluted successively with benzene and benzene-ethyl acetate to obtain the product. (7.142 g, yield: 79.5%)

EXAMPLES 104–109

N-(2-substituted ethyl)-(3-benzyl-5,6,7,8-tetrahydroquinoxaline-2-yl oxy) acetamide:

Benzene (30 ml) in solution with compound 661(1.08 g, 3.0 mM), triethylamine (0.84 m) and a base (6.0 mM) was refluxed. Dilute aqueous potassium carbonate was added to the reaction mixture, and the aqueous layer was extracted three times with chloroform. The organic layer was dried with anhydrous sodium sulfate, and concentrated in vacuo. The residue was charged on a column of silica gel (C-200, 80 g) and eluted successively with benzene and benzene-ethyl acetate (10:1) to obtain the compounds in Table 21.

Table 21 shows the identity of the base and its amount used, the reflux time, the products and the yield in weight and percentage, in each of the above examples. Examples 110–121

Methyl (3-alkyl-5,6,7,8-tetrahydroquinoxaline-2-yl oxy) acetate:

Metallic sodium (1.15 g) was dissolved in anhydrous methanol (100 ml). 2-hydroxy-3,-alkyl-5,6,7,8-tetrahydroquinoxaline (50 mM) was dissolved therein, and methanol was distilled off in vacuo to obtain the sodium salt. Dimethylformamide (100 ml) and methyl chloroacetate (5.43 g, 50 mM) were added thereto and the mixture was stirred at 100° C. The reaction mixture was concentrated in vacuo, and dilute aqueous sodium carbonate was added to the residue, which was then extracted three times with chloroform, and the extract was dried with anhydrous sodium sulfate and concentrated in vacuo. The residue was charged on a column of silica gel (C-200) and eluted successively with benzene and benzene-ethyl acetate- (20:1) to obtain the compounds in Table 22.

Table 22 shows the identity of the starting compound and its amount used, the reaction time, the amount of silica gel used, the products and the yield in weight and percentage in each of the above examples.

EXAMPLES 122–123

2-(2-hydroxyethoxy)-3-alkyl-5,6,7,8-tetrahydroquinoxaline:

The starting compound was dissolved in methanol. 6–8 equivalents of NaBH4 were added several portionwise while refluxing. The reaction mixture was concentrated in vacuo, water was added thereto, then the mixture was extracted three times with chloroform. The extract was dried with anhydrous sodium sulfate and concentrated in vacuo. The residue was charged on a column of silica gel (C-200) and eluted successively with benzene and benzene-ethyl acetate (10:1) to obtain the compounds in Table 23.

Table 23 shows the identity of the starting compound and its amount used, the amount of methanol used, the amount of NaBH4 used, the reflux time, the amount of silica gel used and the product and yield in weight and percentage in each of the above examples.

EXAMPLES 134–185

2-(2-substituted ethoxy)-3-alkyl-5,6,7,8-tetrahydroquinoxaline:

Thionyl chloride (1.3 equivalent) was added dropwise with ice cooling to a starting compound 2-(2-(3–5 mM) dissolved in chloroform and the mixture was stirred at room temperature for 2.5 hours to chlorinate the compound. The reaction mixture was poured into dilute aqueous potassium carbonate and extracted three times with chloroform. The extract, which was dried with anhydrous sodium sulfate, was concentrated in vacuo. Benzene (30 ml), triethylamine (2 equivalents) and a base (2 equivalents) were added to the residue, and the mixture was refluxed. The reaction mixture was poured into dilute aqueous potassium carbonate, and the mixture was extracted three times with chloroform. The extract was dried with anhydrous sodium sulfate and concentrated in vacuo. The residue was charged on a column of silica gel (C-200, 75 g) and eluted successively with chloroform and chloroform-methanol (200:1) to obtain the compounds in Table 24.

Table 24 shows the identity of the starting compound and its amount used, the chlorination reaction time, the base and its amount used, the reflux time, and the product and yield in weight and percentage in each of the above examples.

TABLE 7

| | 2-(substituted carbonylmethoxy)-3,5,6-trimethylpyrazine | | | | |
|---|---|---|---|---|---|
| | Base | | | Yield | Yield |
| Example | name | used (g) | Product | (g) | (%) |
| 7 | 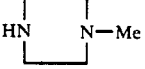 | 0.50 | 066 | 1.12 | 80.5 |
| 8 | 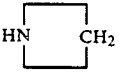 | 0.43 | 067 | 1.10 | 83.6 |
| 9 | 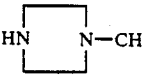 | 0.66 | 068 | 1.23 | 79.8 |
| 10 | H2N—CH2CH2—OH | 0.32 | 069 | 0.88 | 73.6 |
| 11 |  | 0.43 | 070 | 0.91 | 82.0 |
| 12 | 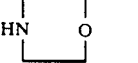 | 0.44 | 075 | 1.10 | 83.0 |

Product is shown by No. of compound hydroxy- ethoxy)-3-alkyl-5,6,7,8-tetrahydroquinoxaline

TABLE 8

| | N-(2-substituted ethyl)-(3,5,6-trimethylpyrazine-2-yloxy)acetamide | | | | | |
|---|---|---|---|---|---|---|
| | Base | | reaction | solvent ratio | Yield | Yield |
| Example | name | used (g) | (time) | (hr.) | product | (g) | (%) |
| 15 | 40% HN (CH3)2 aqueous solution | 8.68 | 1 | 50:1 | 071 | 0.22 | 27.6 |
| 16 |  | 0.53 (6 mM) | 1.5 | 100:1 | 073 | 0.41 | 44.4 |
| 17 |  | 0.43 (5 mM) | 1 | 20:1 | 074 | 0.55 | 59.9 |

TABLE 8-continued

N-(2-substituted ethyl)-(3,5,6-trimethylpyrazine-2-yloxy)acetamide

| Example | Base name | used (g) | reaction (time) (hr.) | solvent ratio | product | Yield (g) | Yield (%) |
|---|---|---|---|---|---|---|---|
| 18 | HN⌐⌐N—CH$_2$CH$_2$OH | 0.78 (6 mM) | 1.5 | 50:1 | 076 | 0.58 | 55.0 |
| 19 | HN⌐⌐NH | 3.44 (40 mM) | 1.5 | 10:1 | 103 | 0.94 | 30.0 |
| 20 | HN⌐⌐N—CH$_3$ | 0.60 (6 mM) | 1 | 50:1 | 105 | 0.27 | 28.0 |
| 21 | H$_2$N—C$_6$H$_{11}$ | 0.60 (6 mM) | 1.5 | 50:1 | 650 | 0.17 | 17.7 | product is shown by No. of compound

TABLE 9

N-(2-substituted ethyl)-(3,5,6-trimethylpyrazine-2-yloxy)acetamide

| Example | BASE name | used (g) | reaction time (hr.) | solvent ratio | Product | Yield (g) | Yield (%) |
|---|---|---|---|---|---|---|---|
| 23 | HN⌐⌐N—CH$_2$Ph—Cl(p) | 1.68 (8 mM) | 8 | 100:1 | 135 | 0.50 | 30.5 |
| 24 | HN⌐⌐N—CH$_2$Ph | 1.41 (8 mM) | 6 | 50:1 | 136 | 0.43 | 27.1 |
| 25 | HN⌐⌐N—CH$_2$Ph—Cl(o) | 1.68 (8 mM) | 8 | 100:1 | 137 | 0.50 | 30.5 | product is shown by No. of compound

TABLE 10

N(2-substituted ethyl)-α-(3-ethyl-5,6-dimethylpyrazine-2-yloxy)-phenylacetamide

| Example | BASE name | used (g) | product | Yield (g) | Yield (%) |
|---|---|---|---|---|---|
| 29 | HN⌐⌐O | 0.70 | 341 | 0.94 | 59.0 |
| 30 | HN⌐⌐N—CH$_2$Ph | 1.41 | 342 | 1.48 | 76.0 |
| 31 | HN⌐⌐N—CH$_2$Ph—Cl(p) | 1.69 | 343 | 1.27 | 60.9 |
| 32 | HN⌐⌐N—CH$_2$Ph—NO$_2$(p) | 1.77 | 344 | 1.32 | 62.0 |
| 33 | HN⌐⌐N—CH$_2$Ph—Cl$_2$(2,4) | 1.96 | 345 | 0.91 | 41.0 |

TABLE 10-continued

N(2-substituted ethyl)-α-(3-ethyl-5,6-dimethylpyrazine-2-yloxy)-phenylacetamide

| Example | BASE name | used (g) | product | Yield (g) | Yield (%) |
|---|---|---|---|---|---|
| 34 | 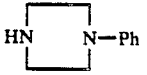 HN⎡⎤N—Ph | 1.30 | 346 | 1.20 | 63.4 |
| 35 | 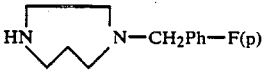 HN⎡⌄⎤N—CH₂Ph—F(p) | 1.67 | 347 | 1.28 | 61.5 |
| 36 | 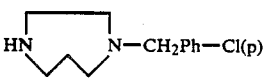 HN⎡⌄⎤N—CH₂Ph—Cl(p) | 1.80 | 348 | 1.77 | 82.6 | product is shown by No. of compound

TABLE 11

N-(2-substituted ethyl)-(3-benzyl-5,6-dimethylpyrazine-2-yloxy)-acetamide

| Example | BASE name | used (g) | reaction (day) | product | Yield (g) | Yield (%) |
|---|---|---|---|---|---|---|
| 40 | 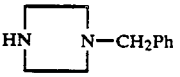 HN⎡⎤N—CH₂Ph | 1.24 | 2 | 376 | 1.54 | 87.8 |
| 41 | 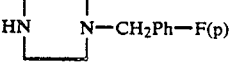 HN⎡⎤N—CH₂Ph—F(p) | 1.48 | 2 | 377 | 1.48 | 81.5 |
| 42 | 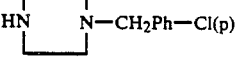 HN⎡⎤N—CH₂Ph—Cl(p) | 1.48 | 2 | 379 | 1.17 | 62.4 |
| 43 | 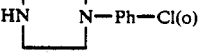 HN⎡⎤N—Ph—Cl(o) | 1.38 | 1 | 381 | 1.29 | 70.7 |
| 44 | 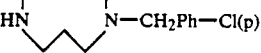 HN⎡⌄⎤N—CH₂Ph—Cl(p) | 1.58 | 2 | 382 | 1.38 | 71.8 |
| 45 |  HN⎡⎤O | 0.61 | 2 | 657 | 0.73 | 50.6 |
| 46 | 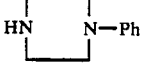 HN⎡⎤N—Ph | 1.14 | 1 | 658 | 1.15 | 67.6 | product is shown by No. of compound

TABLE 12 methyl(3,5,6-trialkylpyrazine-2-yloxy)-acetate

| | starting material | | | | | | | |
|---|---|---|---|---|---|---|---|---|
| | $R_2$ N $R_1$ / $R_3$ N OH | | | used | reaction time | silica-gel | | Yield | Yield |
| Example | $R_1$ | $R_2$ | $R_3$ | (g) | (hr.) | (g) | product | (g) | (%) |
| 47 | Et | Me | Me | 7.60 | 2.5 | 160 | 662 | 9.62 | 85.9 |
| 48 | —CH₂Ph | Me | Me | 10.70 | 2.5 | 210 | 663 | 12.03 | 84.1 |
| 49 | iso-Pro | Me | Me | 8.3 | 2.5 | 160 | 664 | 9.92 | 83.4 |
| 50 | " | Et | Et | 9.70 | 2.5 | 180 | 665 | 12.77 | 96.0 |
| 51 | iso-Bu | Et | Et | 10.40 | 3 | 230 | 666 | 12.86 | 91.9 | product is shown by No. of compound

TABLE 13

2-(2-hydroxyethoxy)-3,5,6-trialkylpyrazine

| Example | starting material name | used g (mM) | methanol (ml) | NaBH₄ (g) | reaction time (hr.) | silica-gel (g) | product | Yield (g) | Yield (%) |
|---|---|---|---|---|---|---|---|---|---|
| 52 | 034 | 17.00(80.95) | 200 | 18.6 | 3.0 | 200 | 679 | 12.84 | 87.2 |
| 53 | 662 | 9.62(42.94) | 200 | 9.9 | 4.0 | 120 | 680 | 7.69 | 91.3 |
| 54 | 663 | 8.75(30.6) | 150 | 9.4 | 2.5 | 160 | 681 | 7.22 | 91.5 |
| 55 | 664 | 19.67(82.65) | 200 | 25.2 | 3.0 | 200 | 682 | 15.51 | 89.4 |
| 56 | 665 | 9.18(34.5) | 150 | 10.5 | 4.0 | 200 | 683 | 7.48 | 91.1 |
| 57 | 666 | 7.32(26.14) | 100 | 8.0 | 3.5 | 160 | 684 | 5.94 | 90.1 | product is shown by No. of compound

TABLE 14

2-(2-substituted ethoxy)-3,5,6-trimethylpyrazine

| Example | BASE name | used (g) | reaction time (hr.) | product | Yield (g) | Yield (%) |
|---|---|---|---|---|---|---|
| 58 | HN☐O (morpholine) | 1.05 | 2.5 | 536 | 0.95 | 63.1 |
| 59 | HN☐CH₂ | 1.10 | 2.5 | 537 | 1.03 | 68.9 |
| 60 | HN☐N—CH₂Ph | 2.02 | 3.0 | 538 | 1.31 | 64.2 |
| 61 | HN☐N—CH₂Ph—Cl (p) | 2.11 | 2.5 | 539 | 1.62 | 72.1 |
| 62 | HN☐N—CH₂Ph—F (p) | 1.94 | 2.0 | 540 | 1.59 | 74.0 |
| 63 | HN☐N—CH₂Ph—Cl (p) | 2.25 | 2.5 | 541 | 1.56 | 66.9 |
| 64 | HN☐N—Bu | 1.70 | 5.0 | 810 | 1.28 | 70.0 |
| 65 | HN☐N—CH₂CH₂—OH | 3.90 | 5.0 | 822 | 1.56 | 94.5 |
| 66 | HNEt₂ | 0.88 | 5.0 | 842 | 0.51 | 35.7 | product is shown by No. of compound

TABLE 15

2-(2-substituted ethoxy)-3-isopropyl-5,6-diethylpyrazine

| Example | BASE name | used (g) | reaction time (hr.) | product | Yield (g) | Yield (%) |
|---|---|---|---|---|---|---|
| 67 | HN☐CH₂ | 0.85 | 3.0 | 550 | 0.83 | 54.4 |
| 68 | HN☐N—Bu | 1.42 | 2.5 | 551 | 0.93 | 51.4 |

TABLE 15-continued

2-(2-substituted ethoxy)-3-isopropyl-5,6-diethylpyrazine

| Example | BASE name | used (g) | reaction time (hr.) | product | Yield (g) | Yield (%) |
|---|---|---|---|---|---|---|
| 69 | HN☐N—CH₂Ph | 1.76 | 3.0 | 552 | 1.05 | 52.8 |
| 70 | HN☐N—CH₂Ph—OMe (p) | 2.20 | 3.0 | 553 | 1.01 | 46.0 |
| 71 | HN☐N—CH₂CH₂—OH | 1.30 | 5.0 | 826 | 1.15 | 66.2 |
| 72 | HNEt₂ | 0.73 | 6.5 | 848 | 0.36 | 25.2 | product is shown by No. of compound

TABLE 16

2-(2-substituted ethoxy)-3-ethyl-5,6-dimethylpyrazine

| Example | Base name | used (g) | reaction time (hr.) | solvent ratio | product | Yield (g) | Yield (%) |
|---|---|---|---|---|---|---|---|
| 73 | HN☐O | 0.87 | 2.5 | 200:1 | 491 | 0.66 | 49.8 |
| 74 | HN☐CH₃ | 0.85 | 2.0 | 200:1 | 492 | 0.79 | 60.1 |
| 75 | HN☐CH—Me | 1.00 | 2.0 | 200:1 | 493 | 0.67 | 48.4 |
| 76 | HN☐N—Me | 1.00 | 2.0 | 30:1 | 494 | 0.84 | 44.6 |
| 77 | HN☐N—CH₂CH₂—OH | 1.20 | 2.0 | 100:1 → 10:1 | 495 | 0.73 | 47.4 |
| 78 | HN☐N—CH₂CH₂—O—CH₂CH₂—OH | 1.74 | 2.0 | 50:1 | 496 | 1.13 | 64.2 |
| 79 | HN☐N—CH₂Ph | 1.68 | 2.0 | 200:1 | 497 | 1.15 | 65.0 |
| 80 | HN☐N—CH₂Ph—Cl (p) | 2.11 | 2.0 | 200:1 | 498 | 1.10 | 56.6 |
| 81 | HN☐N—CH₂Ph—OMe (p) | 2.06 | 2.0 | 200:1 | 499 | 1.17 | 60.9 |
| 82 | HN☐N—CH₂Ph—F (p) | 1.94 | 2.0 | 200:1 | 500 | 1.17 | 62.9 |

TABLE 16-continued 2-(2-substituted ethoxy)-3-ethyl-5,6-dimethylpyrazine

| Example | Base name | used (g) | reaction time (hr.) | solvent ratio | product | Yield (g) | Yield (%) |
|---|---|---|---|---|---|---|---|
| 83 | HN☐N—CH₂Ph—NO₂ (p) | 2.21 | 2.0 | 200:1 | 501 | 1.40 | 70.2 |
| 84 | HN⌇N—CH₂Ph—NO₂ (p) | 2.35 | 2.0 | 200:1 | 502 | 0.62 | 30.0 |
| 85 | HN⌇N—CH₂Ph—F (p) | 2.08 | 2.0 | 200:1 | 503 | 1.00 | 51.8 |
| 86 | HN⌇N—CH₂Ph—Cl (p) | 2.25 | 2.0 | 200:1 | 504 | 1.14 | 56.6 |
| 87 | HN☐N—Bu | 1.42 | 2.0 | 200:1 | 812 | 0.67 | 42.0 |
| 88 | HNEt₂ | 0.73 | 3.0 | 200:1 | 844 | 0.23 | 18.8 | product is shown by No. of compound

TABLE 17

2-(2-substituted ethoxy)-3-benzyl-5,6-dimethylpyrazine

| Example | Base name | used (g) | reaction time (hr.) | solvent ratio | product | Yield (g) | Yield (%) |
|---|---|---|---|---|---|---|---|
| 89 | HN☐O | 0.70 | 2.0 | 200:1 | 511 | 0.57 | 43.6 |
| 90 | HN☐N—CH₂Ph | 1.04 | 2.0 | 200:1 | 512 | 1.04 | 62.5 |
| 91 | HN⌇N—CH₂Ph—Cl (p) | 1.80 | 2.0 | 200:1 | 516 | 1.20 | 64.6 | product is shown by No. of compound

TABLE 18

2-(2-substituted ethoxy)-3-isopropyl-5,6-dimethylpyrazine

| Example | BASE name | used (g) | reaction time (hr.) | solvent ratio | product | Yield (g) | Yield (%) |
|---|---|---|---|---|---|---|---|
| 92 | HN☐O | 0.87 | 2.5 | 200:1 | 544 | 0.89 | 63.8 |
| 93 | HN☐N—CH₂Ph—Cl (p) | 2.11 | 2.5 | 200:1 | 546 | 1.57 | 80.8 |
| 94 | HN⌇N—CH₂Ph—Cl (p) | 2.25 | 2.5 | 200:1 | 547 | 1.42 | 68.2 |
| 95 | HN☐N—Bu | 1.43 | 3.0 | 200:1 | 697 | 0.94 | 56.3 |

TABLE 18-continued

2-(2-substituted ethoxy)-3-isopropyl-5,6-dimethylpyrazine

| Example | BASE name | used (g) | reaction time (hr.) | solvent ratio | product | Yield (g) | Yield (%) |
|---|---|---|---|---|---|---|---|
| 96 | HN⌐⌐N—Bu | 1.43 | 2.0 | 200:1 | 814 | 0.77 | 46.0 |
| 97 | HN⌐⌐N—CH₂CH₂—OH | 1.30 | 2.5 | 200:1 | 825 | 1.24 | 77.0 |
| 98 | HN⌐⌐CH₂ | 0.85 | 5.0 | 200:1 | 834 | 1.17 | 68.3 |
| 99 | HNEt₂ | 0.73 | 18.0 | 200:1 | 846 | 0.12 | 11.2 | product is shown by No. of compound

TABLE 19

2-(2-substituted ethoxy)-3-isobutyl-5,6-diethylpyrazine

| Example | BASE name | used (g) | reaction time (hr.) | product | Yield (g) | Yield (%) |
|---|---|---|---|---|---|---|
| 99 | HN⌐⌐N—CH₂Ph | 1.76 | 3.5 | 556 | 0.45 | 21.9 |
| 100 | HN⌐⌐N—CH₂Ph—OMe (p) | 2.20 | 4.0 | 558 | 0.77 | 33.9 | product is shown by No. of compound

TABLE 20

2-hydroxy-3-alkyl-5,6,7,8-tetrahydroquinoxaline $R_1$—CHCONH₂ + cyclohexane-1,2-dione → tetrahydroquinoxaline-2-ol
|
NH₂·HCl

| Reference example | amino acidamide HCl used (g) | $R_1$ | Product Yield (g) | Yield (%) |
|---|---|---|---|---|
| 5 | 7.63 | Pro | 4.75 | 50.0 |
| 6 | 7.63 | iso-Pro | 4.95 | 51.6 |
| 7 | 8.32 | Bu | 7.49 | 73.0 |
| 8 | 8.32 | iso-Bu | 6.58 | 64.0 |
| 9 | 8.32 | sec-Bu | 6.58 | 64.0 |
| 10 | 9.04 | —(CH₂)₄CH₃ | 9.03 | 82.0 |
| 11 | 9.74 | —(CH₂)₅CH₃ | 7.81 | 66.7 |
| 12 | 10.44 | —(CH₂)₆CH₃ | 9.33 | 75.0 |
| 13 | 11.14 | —(CH₂)₇CH₃ | 11.67 | 89.1 |
| 14 | 11.83 | —(CH₂)₈CH₃ | 10.50 | 72.4 |
| 15 | 12.55 | —(CH₂)₉CH₃ | 12.73 | 92.2 |
| 16 | 13.95 | —(CH₂)₁₁CH₃ | 14.00 | 88.1 |
| 17 | 15.35 | —(CH₂)₁₃CH₃ | 16.58 | 95.8 |
| 18 | 16.75 | —(CH₂)₁₅CH₃ | 18.55 | 99.2 |

TABLE 21

N-(2-substituted ethyl)-(3-benzyl-5,6,7,8-tetrahydroquinoxaline-2-yloxy)-acetamide

| Example | BASE name | used (g) | reaction time (day) | Product No. of comp | Yield (g) | Yield (%) |
|---|---|---|---|---|---|---|
| 104 | HN⌐⌐N—CH₂Ph | 1.06 | 1 | 368 | 1.00 | 66.8 |

TABLE 21-continued

N-(2-substituted ethyl)-(3-benzyl-5,6,7,8-tetrahydroquinoxaline-2-yloxy)-acetamide

| Example | BASE name | used (g) | reaction time (day) | Product No. of comp | Yield (g) | Yield (%) |
|---|---|---|---|---|---|---|
| 105 | HN⟨ ⟩N—CH$_2$Ph—OMe (p) 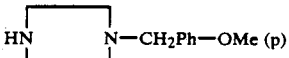 | 1.24 | 4 | 369 | 1.38 | 87.0 |
| 106 | HN⟨ ⟩N—CH$_2$Ph—Cl (p) 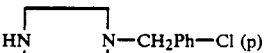 | 1.27 | 2 | 370 | 1.07 | 67.0 |
| 107 | HN⟨ ⟩N—Ph—Cl (o) 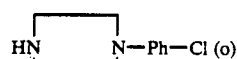 | 1.18 | 3 | 371 | 1.36 | 87.3 |
| 108 | HN⟨ ⟩N—CH$_2$Ph—F (p)  | 1.25 | 3 | 372 | 1.21 | 76.0 |
| 109 | HN⟨ ⟩N—Ph 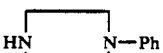 | 0.73 | 2 | 373 | 0.73 | 50.2 |

TABLE 22 methyl(3-alkyl-5,6,7,8-tetrahydroquinoxaline-2-yloxy)-acetate

| Example | starting compound N OH N R$_1$ R$_1$ | used (g) | reaction time (hr.) | silica-gel (g) | Product No. of compound | Yield (g) | Yield (%) |
|---|---|---|---|---|---|---|---|
| 110 | Bu | 10.30 | 3 | 210 | 667 | 11.54 | 83.2 |
| 111 | —(CH$_2$)$_4$CH$_3$ | 10.10 | 3 | 210 | 668 | 11.64 | 79.7 |
| 112 | —(CH$_2$)$_5$CH$_3$ | 11.70 | 2.5 | 210 | 669 | 12.24 | 80.0 |
| 113 | —(CH$_2$)$_6$CH$_3$ | 12.40 | 2.5 | 210 | 670 | 13.35 | 83.5 |
| 114 | —(CH$_2$)$_7$CH$_3$ | 13.10 | 3 | 200 | 671 | 13.02 | 78.0 |
| 115 | —(CH$_2$)$_8$CH$_3$ | 13.80 | 3 | 240 | 672 | 13.71 | 78.8 |
| 116 | —(CH$_2$)$_9$CH$_3$ | 14.50 | 2.5 | 210 | 673 | 13.61 | 75.2 |
| 117 | —(CH$_2$)$_{11}$CH$_3$ | 15.90 | 3 | 280 | 674 | 16.00 | 82.1 |
| 118 | —(CH$_2$)$_{13}$CH$_3$ | 17.30 | 3 | 280 | 675 | 16.33 | 78.1 |
| 119 | —(CH$_2$)$_{15}$CH$_3$ | 18.70 | 2.5 | 340 | 676 | 18.74 | 84.0 |
| 120 | Pro | 9.60 | 3 | 220 | 677 | 10.29 | 78.0 |
| 121 | sec-Bu | 10.30 | 2.5 | 260 | 678 | 11.73 | 84.4 |

TABLE 23

2-(2-hydroxyethoxy)-3-alkyl-5,6,7,8-tetrahydroquinoxaline

| Example | starting compound No. of comp | used g (mM) | methanol (ml) | NaBH$_4$ (g) | reaction time (hr.) | silica-gel (g) | Product No. of comp | Yield (g) | Yield (%) |
|---|---|---|---|---|---|---|---|---|---|
| 122 | 667 | 12.40(44.6) | 200 | 10.2 | 2.5 | 200 | 685 | 10.63 | 95.3 |
| 123 | 668 | 9.07(31.1) | 200 | 7.2 | 3.0 | 200 | 686 | 7.12 | 86.7 |
| 124 | 669 | 9.55(31.2) | 200 | 9.6 | 2.5 | 200 | 687 | 7.95 | 91.7 |
| 125 | 670 | 9.70(30.3) | 200 | 9.3 | 3.0 | 200 | 688 | 8.05 | 91.0 |
| 126 | 671 | 11.10(33.2) | 300 | 7.8 | 3.0 | 250 | 689 | 9.31 | 91.6 |
| 127 | 672 | 9.50(27.3) | 250 | 9.4 | 3.0 | 250 | 690 | 8.20 | 93.9 |
| 128 | 673 | 10.80(29.8) | 250 | 9.1 | 2.5 | 250 | 691 | 9.15 | 92.0 |
| 129 | 674 | 9.54(24.46) | 250 | 7.5 | 3.0 | 200 | 692 | 7.94 | 89.7 |
| 130 | 675 | 9.56(22.9) | 250 | 6.9 | 3.0 | 200 | 693 | 8.63 | 96.6 |
| 131 | 676 | 9.17(32.9) | 250 | 6.2 | 3.0 | 200 | 694 | 7.27 | 84.6 |
| 132 | 677 | 7.78(29.47) | 200 | 9.0 | 3.0 | 200 | 695 | 6.60 | 95.0 |
| 133 | 678 | 7.50(27.0) | 200 | 8.4 | 2.5 | 170 | 696 | 5.77 | 85.5 |

TABLE 24

2-(2-substituted ethoxy-3-alkyl-5,6,7,8-tetrahydroquinoxaline

| Example | starting compound No. of comp | used g | chlorination time (hr) | BASE name | used g | reflux time (hr.) | product No. of comp | Yield (g) | Yield (%) |
|---|---|---|---|---|---|---|---|---|---|
| 134 | 685 | 1.25 (5 mM) | 3.0 | HN⎯O (morpholine) | 0.87 (10 mM) | 2.0 | 517 | 1.38 | 86.5 |
| 135 | 685 | 1.00 (4 mM) | 3.0 | HN⎯N—CH₂Ph | 1.42 (8 mM) | 2.0 | 518 | 1.23 | 75.4 |
| 136 | 685 | 1.00 (4 mM) | 3.0 | HN⎯N—CH₂Ph—Cl (p) | 1.69 (8 mM) | 2.0 | 519 | 0.89 | 50.3 |
| 137 | 685 | 1.00 (4 mM) | 3.0 | HN⎯N—CH₂Ph—Cl (p) | 1.80 (8 mM) | 2.5 | 520 | 1.00 | 54.8 |
| 138 | 686 | 1.32 (5 mM) | 3.5 | HN⎯O | 0.87 (10 mM) | 3.0 | 559 | 0.92 | 55.3 |
| 139 | 686 | 1.32 (5 mM) | 3.5 | HN⎯N—Bu | 1.42 (10 mM) | 2.5 | 560 | 1.01 | 52.1 |
| 140 | 686 | 1.32 (5 mM) | 3.5 | HN⎯N—CH₂Ph | 1.76 (10 mM) | 3.0 | 561 | 1.27 | 60.2 |
| 141 | 686 | 1.32 (5 mM) | 3.5 | HN⎯N—CH₂Ph—F (p) | 2.08 (10 mM) | 2.5 | 562 | 1.24 | 54.6 |
| 142 | 687 | 1.39 (5 mM) | 3.5 | HN⎯O | 0.87 (10 mM) | 3.0 | 564 | 0.99 | 57.1 |
| 143 | 687 | 1.39 (5 mM) | 3.5 | HN⎯N—Bu | 1.42 (10 mM) | 3.0 | 565 | 1.11 | 55.2 |
| 144 | 687 | 1.39 (5 mM) | 3.5 | HN⎯N—CH₂Ph | 1.76 (10 mM) | 2.5 | 567 | 1.25 | 57.3 |
| 145 | 687 | 1.39 (5 mM) | 3.5 | HN⎯N—CH₂Ph—Cl (p) | 2.10 (10 mM) | 2.5 | 568 | 1.62 | 68.9 |
| 146 | 687 | 1.39 (5 mM) | 3.5 | HN⎯N—CH₂Ph—F (p) | 2.08 (10 mM) | 2.5 | 569 | 1.29 | 55.4 |
| 147 | 688 | 1.17 (4 mM) | 3.0 | HN⎯N—Bu | 1.14 (8 mM) | 2.5 | 571 | 1.01 | 60.7 |
| 148 | 689 | 1.53 (5 mM) | 3.0 | HN⎯O | 0.87 (10 mM) | 2.0 | 572 | 1.06 | 56.5 |

TABLE 24-continued 2-(2-substituted ethoxy-3-alkyl-5,6,7,8-tetrahydroquinoxaline

| Example | starting compound | | chlorin-ation time (hr) | BASE | | reflux time (hr.) | product | | |
|---|---|---|---|---|---|---|---|---|---|
| | No. of comp | used g | | name | used g | | No. of comp | Yield (g) | Yield (%) |
| 149 | 689 | 1.23 (4 mM) | 3.0 |  HN N—Bu | 1.14 (8 mM) | 2.0 | 573 | 0.87 | 50.6 |
| 150 | 689 | 1.23 (4 mM) | 3.0 |  HN N—CH₂Ph | 1.42 (8 mM) | 2.0 | 574 | 0.95 | 52.9 |
| 151 | 689 | 1.23 (4 mM) | 3.0 |  HN N—CH₂Ph—Cl (p) | 1.68 (8 mM) | 2.0 | 575 | 0.65 | 32.6 |
| 152 | 689 | 1.23 (4 mM) | 3.0 | 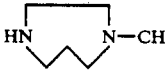 HN N—CH₂Ph—F (p) | 1.67 (8 mM) | 2.5 | 576 | 0.57 | 28.7 |
| 153 | 690 | 1.60 (5 mM) | 3.5 | 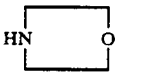 HN O | 0.87 (10 mM) | 2.0 | 579 | 0.63 | 32.4 |
| 154 | 690 | 1.28 (4 mM) | 3.5 | 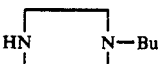 HN N—Bu | 1.14 (8 mM) | 2.5 | 580 | 0.54 | 30.4 |
| 155 | 690 | 1.28 (4 mM) | 3.5 | 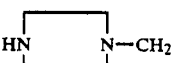 HN N—CH₂Ph | 1.41 (8 mM) | 2.0 | 581 | 0.84 | 43.9 |
| 156 | 690 | 1.28 (4 mM) | 3.5 | 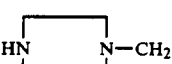 HN N—CH₂Ph—OMe (p) | 1.65 (8 mM) | 2.0 | 582 | 1.01 | 47.8 |
| 157 | 690 | 1.28 (4 mM) | 3.5 | 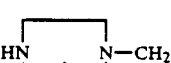 HN N—CH₂Ph—Cl (p) | 1.80 (8 mM) | 2.5 | 583 | 0.78 | 37.0 |
| 158 | 691 | 1.67 (5 mM) | 3.0 | 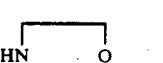 HN O | 0.87 (10 mM) | 2.0 | 585 | 0.79 | 39.2 |
| 159 | 691 | 1.34 (4 mM) | 3.0 | 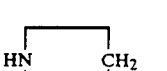 HN CH₂ | 0.68 (8 mM) | 2.5 | 586 | 0.65 | 40.5 |
| 160 | 691 | 1.34 (4 mM) | 3.0 | 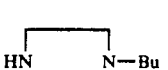 HN N—Bu | 1.14 (8 mM) | 2.5 | 587 | 0.77 | 42.0 |
| 161 | 691 | 1.34 (4 mM) | 3.0 | 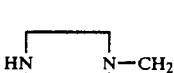 HN N—CH₂CH₂—OH | 1.04 (8 mM) | 2.5 | 588 | 0.58 | 32.5 |
| 162 | 691 | 1.34 (4 mM) | 3.0 | 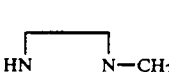 HN N—CH₂Ph | 1.41 (8 mM) | 2.5 | 589 | 0.93 | 47.3 |
| 163 | 691 | 1.34 (4 mM) | 3.0 | 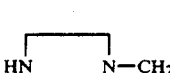 HN N—CH₂Ph—Cl (p) | 1.68 (8 mM) | 2.5 | 590 | 1.07 | 50.8 |

TABLE 24-continued 2-(2-substituted ethoxy-3-alkyl-5,6,7,8-tetrahydroquinoxaline

| Example | starting compound No. of comp | used g | chlorin- ation time (hr) | BASE name | used g | reflux time (hr.) | product No. of comp | Yield (g) | Yield (%) |
|---|---|---|---|---|---|---|---|---|---|
| 164 | 691 | 1.34 (4 mM) | 3.0 | HN⎯N—CHPh₂ | 2.01 (8 mM) | 2.5 | 591 | 1.17 | 51.5 |
| 165 | 691 | 1.34 (4 mM) | 3.0 | HN⎯N—CH₂Ph—F (p) | 1.67 (8 mM) | 2.0 | 592 | 0.70 | 33.4 |
| 166 | 692 | 1.09 (3 mM) | 4.5 | HN⎯O | 0.53 (6 mM) | 3.0 | 594 | 0.64 | 49.5 |
| 167 | 692 | 1.09 (3 mM) | 5.0 | HN⎯N—Bu | 0.86 (6 mM) | 2.5 | 595 | 0.84 | 57.6 |
| 168 | 692 | 1.09 (3 mM) | 5.0 | HN⎯N—CH₂Ph | 1.06 (6 mM) | 2.5 | 596 | 0.92 | 59.0 |
| 169 | 692 | 1.09 (3 mM) | 5.0 | HN⎯N—CH₂Ph—OMe (p) | 1.24 (6 mM) | 2.5 | 597 | 0.93 | 56.4 |
| 170 | 692 | 1.09 (3 mM) | 4.5 | HN⎯N—CH₂Ph—F (p) | 1.25 (6 mM) | 2.5 | 598 | 0.83 | 50.1 |
| 171 | 693 | 1.17 (3 mM) | 5.0 | HN⎯N—Bu | 0.86 (6 mM) | 2.5 | 600 | 0.74 | 48.0 |
| 172 | 693 | 1.17 (3 mM) | 5.0 | HN⎯N—CH₂Ph | 1.06 (6 mM) | 2.5 | 601 | 0.84 | 51.1 |
| 173 | 693 | 1.17 (3 mM) | 5.0 | HN⎯N—CH₂Ph—F (p) | 1.17 (6 mM) | 2.5 | 602 | 0.93 | 54.8 |
| 174 | 693 | 1.17 (3 mM) | 5.0 | HN⎯N—CH₂Ph—Cl (p) | 1.35 (6 mM) | 2.5 | 603 | 0.92 | 51.4 |
| 175 | 693 | 1.17 (3 mM) | 5.0 | HN⎯N—CHPh₂ | 1.51 (6 mM) | 2.5 | 604 | 0.65 | 34.7 |
| 177 | 694 | 1.26 (3 mM) | 4.5 | HN⎯N—Bu | 0.86 (6 mM) | 2.5 | 607 | 0.86 | 52.9 |
| 178 | 694 | 1.26 (3 mM) | 5.0 | HN⎯N—CH₂Ph | 1.06 (6 mM) | 2.0 | 608 | 0.88 | 50.9 |
| 179 | 694 | 1.26 (3 mM) | 4.5 | HN⎯N—CH₂Ph—OMe (p) | 1.32 (6 mM) | 2.5 | 609 | 0.95 | 51.1 |

TABLE 24-continued

| | | 2-(2-substituted ethoxy-3-alkyl-5,6,7,8-tetrahydroquinoxaline | | | | | | |
|---|---|---|---|---|---|---|---|---|
| | starting compound | | chlorin- | | | reflux | product | |
| Exam- | No. of | | ation | BASE | | time | No. of | Yield | Yield |
| ple | comp | used g | time (hr) | name | used g | (hr.) | comp | (g) | (%) |
| 180 | 685 | 1.25 (5 mM) | 6.0 | HN N—Bu | 1.42 (10 mM) | 5.0 | 817 | 1.10 | 59.0 |
| 181 | 689 | 0.77 (2.5 mM) | 5.5 | HN N—CH₂CH₂—OH | 1.60 (12.3 mM) | 5.0 | 830 | 0.45 | 43.1 |
| 182 | 685 | 1.18 (4.7 mM) | 6.5 | HN CH₂ | 0.85 (10 mM) | 5.0 | 837 | 0.89 | 56.3 |
| 183 | 689 | 0.77 (2.5 mM) | 6.0 | HN CH₂ | 0.43 (5 mM) | 6.0 | 839 | 0.61 | 65.1 |
| 184 | 685 | 1.25 (5 mM) | 5.0 | HNEt₂ | 1.46 (20 mM) | 24 | 850 | 0.38 | 25.0 |
| 185 | 689 | 0.77 (2.5 mM) | 7.0 | HNEt₂ | 0.73 (10 mM) | 24 | 851 | 0.47 | 52.1 |

TABLE 25

NMR spectrum, Mass spectrum and Rf-value on silica-gel layer chromatography

| Comp. No. | NMR (CDCl₃, inner standard TMS) ppm | MASS | Rf |
|---|---|---|---|
| 034 | 2.34(3H, s), 2.40(3H, s), 2.46(3H, s), 3.76(3H, s), 4.89(2H, s) | 211 | |
| 035 | 1.53(3H, d, J=6.9), 2.28(3H, s), 2.34(3H×2, s), 3.65(3H, s), 5.17 (1H, q, J=6.9) | 225 | |
| 036 | 2.36(3H, s), 2.41(3H, s), 2.51(3H, s), 3.70(3H, s), 6.11(1H, s), 7.3–7.6(5H, m) | 287 | |
| 037 | 2.30(3H, s), 2.35(6H, s), 4.83(2H, s) | 197 | |
| 038 | 1.66(2H, d, J=7.1), 2.32(3H, s), 2.38(3H, s), 2.45(3H, s), 5.27 (1H, q, J=7.1) | 211 | |
| 039 | 2.33(3H, s), 2.35(3H, s), 2.38(3H, s), 6.05(1H, s), 7.3–7.6(5H, m) | 273 | |
| 066 | 2.32(3H, s), 2.35(3H, s), 2.39(3H, s), 2.46(3H, s), 2.3–2.5(4H, m) | 279, 179 | |
| 067 | 1.5–1.7(3H×2), 2.35(3H, s), 2.39(3H, s), 2.47(3H, s), 3.3–3.7 (4H, m), 4.99(2H, s) | 263, 179 | |
| 068 | 2.35(3H, s), 2.39(3H, s), 2.46(3H, s), 2.2–2.7(6H, m), 3.4–3.7 (4H, m), 4.99(2H, s) | 309, 179 | |
| 069 | 2.37(3H, s), 2.41(3H, s), 2.45(3H, s), 3.3–3.6(2H, m), 3.75(2H, t, J≈4.7), 4.84(2H, s), 6.86(1H, bs) | 240, 179 | |
| 070 | 2.35(3H×2, s), 2.40(3H×2, s), 2.47(3H×2, s), 3.6(8H, bs), 5.02 (4H, s) | 443, 180 179 | |
| 071 | 2.21(3H×2, s), 2.38(3H, s), 2.42(3H, s), 2.47(3H, s), 3.1–3.5(4H, m), 4.83(2H, s), 7.0(1H, bs) | 267 | |
| 072 | 2.37(3H, s), 2.42(3H, s), 2.48(3H, s), 3.07(2H, t, J≈6.1), 3.54 (2H, t, J≈6.1), 79(2H, s), 6.8(1H, bs), 7.0–7.4(5H, m) | 332, 179 | |
| 073 | 2.38(3H, s), 2.42(3H, s), 2.51(3H, s), 2.3–2.6(6H, m), 3.42(2H, q, J≈5.7), 3.5–3.8(4H, m), 4.84(2H, s) | 309, 240 179 | |
| 074 | 1.3–1.7(6H, m), 2.38(3H, s), 2.42(3H, s), 2.50(3H, s), 2.2–2.5 (6H, m), 3.41(2H, sext, J≈5.6), 3.76(1H, t, J≈5.6), 4.84(2H, s) | 307, 240 179 | |
| 075 | 2.36(3H, s), 2.40(3H, s), 2.47(3H, s), 3.4–3.8(8H, m), 4.99(2H, s) | 266, 179 | |
| 076 | 2.42(3H, s), 2.46(3H, s), 2.50(3H, s), 2.3–2.6(12H, m), 3.40(2H, q, J≈6), 3.62(2H, t, J≈5.2), 4.84(2H, s) | 352 | |
| 103 | 2.38(3H, s), 2.42(3H, s), 2.51(3H, s), 2.3–2.6(6H, m), 2.7–2.9 (4H, m), 3.41(2H, q, J≈5.5), 4.84(2H, s), 7.0(1H, bs) | 308 | |
| 105 | 2.26(3H, s), 2.38(3H, s), 2.43(3H, s), 2.51(3H, s), 3.2–3.5(4H, m), 4.84(2H, s), 7.0(1H, bs) | 322, 113 | |
| 135 | 2.37(3H, s), 2.43(3H, s), 2.51(3H, s), 2.2–2.6(10H, m), 3.2–3.5 (2H, m), 3.42(2H, s), 4.83(2H, s), 7.26(4H, s) | 434, 432 223, 125 | |
| 136 | 2.26(3H, s), 2.38(3H, s), 2.50(3H, s), 2.2–2.6(10H, m), 3.2–3.5 (2H, m), 3.48(2H, s), 4.83(2H, s), 7.30(5H, s) | 398, 304 189 | |
| 137 | 2.38(3H, s), 2.44(3H, s), 2.46(3H, s), 2.3–2.6(10H, m), 2.3–3.5 (2H, m), 3.60(2H, s), 4.84(2H, s), 6.9–7.5(4H, m) | 434, 432 223, 125 | |
| 341 | 1.33(3H, t, J=7.4), 1.74(2H, br. s), 2.35(3H, s), 2.40(3H, s), 2.3–2.6(4H, m), 2.92(2H, q, J=7.4), 3.2–3.5(2H, m), 3.5–3.7(4H, m), 6.44(1H, s), 7.0(1H, br. s), 7.2–7.7(5H, m) | 399 | |
| 342 | 1.33(3H, t, J=7.4), 1.77(4H, br. s), 2.34(3H, s), 2.40(3H, s), 2.3–2.6(6H, m), 2.91(2H, q, J=7.4), 3.2–3.5(2H, m), 3.49(2H, s), 6.42 (1H, s), 7.0–7.7(11H, m) | 488, 189 | |
| 343 | 1.33(3H, t, J=7.4), 1.6(4H, br. s), 2.34(3H, s), 2.40(3H, s), 2.2–2.8(6H, m), 2.92(2H, q, J=7.4), 3.2–3.5(2H, m), 3.43(2H, s), 6.42 (1H, s), 7.26(1H, s), 7.2–7.6(5H, m) | 524, 522 223 | |

TABLE 25-continued

NMR spectrum, Mass spectrum and Rf-value on silica-gel layer chromatography

| Comp. No. | NMR (CDCl$_3$, inner standard TMS) ppm | MASS | Rf |
|---|---|---|---|
| 344 | 1.34(3H, t, J=7.4), 1.66(4H, br. s), 2.35(3H, s), 2.40(3H, s), 2.2–2.6(6H, m), 2.92(2H, q, J=7.4), 3.2–3.5(2H, m), 2.56(2H, s), 6.43 (1H, s), 7.0(1H, br. s), 7.2–7.7(7H, m), 8.18(2H, d, J=8.8) | 533, 234 | |
| 345 | 1.34(3H, t, J=7.4), 1.90(2H, br. s), 2.34(3H, s), 2.41(3H, s), 2.2–2.6(8H, m), 2.92(2H, q, J=7.4), 3.2–3.5(2H, m), 3.55(2H, s), 6.43 (1H, s), 7.0–7.7(9H, m) | 560, 558 556, 258 256 | |
| 346 | 1.34(3H, t, J=7.4), 1.73(2H, br. s), 2.35(3H, s), 2.38(3H, s), 2.3–2.6(6H, m), 2.88(2H, q, J=7.4), 3.0–3.2(2H, m), 3.3–3.5(2H, m), 6.45(1H, s), 6.7–7.7(10H, m) | 474, 330 175 | |
| 347 | 1.31(3H, t, J=7.4), 1.6–2.1(4H, m), 2.34(3H, s), 2.40(3H, s), 2.2–2.8(8H, m), 2.90(2H, q, J=7.4), 3.2–3.5(2H, m), 3.54(2H, s), 6.43 (1H, s), 6.8–7.7(10H, m) | 521, 520 221 | |
| 348 | 1.31(3H, t, J=7.4), 1.6–2.1(2H, m), 2.34(3H, s), 2.40(3H, s), 2.4–2.8(12H, m), 3.1–3.5(2H, m), 3.54(2H, s), 6.43(1H, s), 7.26(4H, s), 7.2–7.6(5H, m) | 538, 536 239, 237 | |
| 376 | 1.23(3H×2, t, J≈7.6), 1.4–2.2(8H, m), 2.2–3.6(10H, m), 4.21(4H, s), 4.83(2H, s), 6.51(1H, br. s), 7.0–7.4(10H, m) | 487, 174 | 0.44 |
| 377 | 1.22(3H, t, J≈7.6), 1.26(3H, t, J=7.6), 1.6–2.0(2H, m), 2.2–2.5 (8H, m), 2.69(2H, q, J≈7.6), 2.77(2H, q, J≈7.6), 3.1–3.6(2H, m), 3.36(2H, s), 4.18(2H, s), 4.81(2H, s), 6.4(1H, br. s), 6.8–7.4(9H, m) | 520, 207 | 0.38 |
| 379 | 1.22(3H, t, J≈7.6), 1.26(3H, t, J=7.6), 1.6–2.0(2H, m), 2.2–3.0 (14H, m), 3.0–3.6(2H, m), 3.36(2H, s), 4.18(2H, s), 4.81(2H, s), 6.4(1H, br. s), 7.0–7.4(9H, m) | 538, 536 225, 223 | 0.40 |
| 381 | 1.23(2H×2, t, J≈7.6), 1.6–1.8(2H, m), 2.2–3.0(14H, m), 3.0–3.5 (2H, m), 4.19(2H, s), 4.84(2H, s), 6.51(1H, br. s), 6.8–7.4(9H, m) | 524, 522 | 0.62 |
| 382 | 1.22(3H, t, J≈7.6), 1.25(3H×2, t, J≈7.6), 1.4–2.0(2H, m), 2.2–3.0(14H, m), 3.0–3.4(2H, m), 3.50(2H, s), 4.07(2H, s), 4.81(2H, s), 6.4(1H, br. s), 7.0–7.4(9H, m) | 552, 550 343, 237 | 0.37 |
| 491 | 1.23(3H, t, J≈7.6), 2.32(3H×2), 2.3–3.0(8H, m), 3.6–3.8(4H, m), 4.0–4.3(2H, m) | 266, 114 | 0.33 |
| 492 | 1.23(3H, t, J=7.4), 1.3–2.0(6H, m), 2.31(3H, s), 2.33(2H, s), 2.5–3.0(8H, m), 4.2–4.5(2H, m) | 264, 179 | 0.28 |
| 493 | 0.9–1.2(3H, m), 1.23(3H, t, J≈7.4), 1.3–2.0(5H, m), 2.31(3H, s), 2.33(3H, s), 2.5–3.0(8H, m), 4.2–4.5(2H, m) | 278, 111 | 0.29 |
| 494 | 1.23(3H, t, J=7.4), 2.30(3H×2, s), 2.31(3H, s), 2.3–3.0(12H, m), 4.0–4.3(2H, m) | 279, 113 | 0.15 |
| 495 | 1.22(3H, t, J≈7.4), 2.31(3H×2, s), 2.3–3.0(14H, m), 3.62(2H, t, J=5.4), 4.0–4.3(2H, m) | 309, 143 | 0.06 |
| 496 | 1.23(3H, t, J=7.4), 2.31(3H×2, s), 2.3–3.0(14H, m), 3.5–3.8(6H, m), 4.0–4.3(3H, m) | 353, 187 | 0.11 |
| 497 | 1.22(3H, t, J≈7.4), 2.31(3H×2, s), 2.3–3.0(12H, m), 3.52(2H, s), 4.0–4.3(2H, m), 7.30(5H, s) | 355, 189 | 0.38 |
| 498 | 1.22(3H, t, J≈7.4), 2.31(3H×2, s), 2.3–3.0(12H, m), 3.48(2H, s), 4.0–4.3(2H, m), 7.29(4H, s) | 391, 389 223 | 0.36 |
| 499 | 1.22(3H, t, J≈7.4), 2.31(3H×2, s), 2.3–3.0(12H, m), 3.46(2H, s), 3.79(3H, s), 4.0–4.3(2H, m), 6.84(2H, d, J=8.6), 7.22(2H, d, J=8.6) | 385, 219 | 0.33 |
| 500 | 1.22(3H, t, J=7.4), 2.31(3H×2, s), 2.3–3.0(12H, m), 3.47(2H, s), 4.0–4.3(2H, m), 6.8–7.4(4H, m) | 373, 207 | 0.35 |
| 501 | 1.22(3H, t, J≈7.4), 2.31(3H, s), 2.33(3H, s), 2.3–3.0(12H, m), 3.59(2H, s), 4.0–4.2(2H, m), 7.50(2H, d, J=8.8), 8.17(2H, d, J=8.8) | 400, 234 | 0.39 |
| 502 | 1.23(3H, t, J≈7.4), 1.6–2.0(2H, m), 2.31(3H, s), 2.33(3H, s), 2.5–3.0(12H, m), 3.72(2H, s), 4.0–4.3(2H, m), 7.51(2H, d, J≈8.8), 8.19(2H, d, J≈8.8) | 414, 248 | 0.28 |
| 503 | 1.23(3H, t, J≈7.4), 1.6–2.0(2H, m), 2.31(3H×2, s), 2.5–3.0(12H, m), 3.60(2H, s), 4.0–4.3(2H, m), 6.8–7.4(4H, m) | 387 | 0.20 |
| 504 | 1.22(3H, t, J≈7.4), 1.6–2.0(2H, m), 2.31(3H×2, s), 2.5–3.0(12H, m), 7.27(4H, s) | 405, 403 237 | 0.23 |
| 511 | 2.31(3H×2, s), 2.4–2.7(6H, m), 3.6–3.8(4H, m), 4.0–4.3(2H, s), 7.1–7.5(5H, m) | 328, 114 | 0.41 |
| 512 | 2.30(3H×2, s), 2.3–2.7(10H, m), 3.51(2H, s), 4.0–4.2(2H, m), 4.08(2H, s), 7.1–7.5(10H, m) | 417, 202 189 | 0.37 |
| 516 | 1.6–2.0(2H, m), 2.30(3H×2, s), 2.5–3.0(10H, m), 3.58(2H, s), 3.9–4.2(2H, m), 4.08(2H, s), 7.1–7.5(10H, m) | 467, 465 251, 237 | 0.24 |
| 536 | 2.30(3H, s), 2.34(3H, s), 2.41(3H, s), 2.4–2.7(6H, m), 3.6–3.8 (4H, m), 4.0–4.3(2H, m) | 252, 101 | 0.30 |
| 537 | 1.2–1.8(6H, m), 2.30(3H, s), 2.36(3H, s), 2.41(3H, s), 2.4–2.8 (6H, m), 4.1–4.3(2H, m) | 250, 111 | 0.20 |
| 538 | 2.29(3H, s), 2.32(3H, s), 2.40(3H, s), 2.3–2.8(10H, m), 3.52(2H, s), 4.0–4.3(2H, m), 7.30(5H, s) | 341, 189 | 0.27 |
| 539 | 2.30(3H, s), 2.32(3H, s), 2.41(3H, s), 2.3–2.8(10H, m), 3.47(2H, s), 4.0–4.3(2H, m), 7.26(4H, s) | 377, 375 223 | 0.27 |
| 540 | 2.30(3H, s), 2.33(3H, s), 2.41(3H, s), 2.4–2.8(10H, m), 3.48(2H, s), 4.0–4.3(2H, m), 6.8–7.4(4H, m) | 359, 220 207 | 0.20 |
| 541 | 1.6–2.0(2H, m), 2.30(3H, s), 2.32(3H, s), 2.41(3H, s), 2.5–3.0 (10H, m), 3.60(2H, s), 4.0–4.3(2H, m), 7.26(4H, s) | 391, 389 237, 165 | 0.17 |
| 544 | 1.20(3H×2, d, J=6.8), 2.32(3H×2, s), 2.4–2.8(6H, m), 3.42(1H, sept, J=6.8), 3.5–3.8(4H, m), 4.0–4.3(2H, m) | 280, 114 | 0.33 |

TABLE 25-continued

| Comp. No. | NMR (CDCl₃, inner standard TMS) ppm | MASS | Rf |
|---|---|---|---|
| 546 | 1.20(3H×2, d, J=6.8), 2.30(3H×2, s), 2.2–2.8(10H, m), 3.42(1H, sept, J=6.8), 3.47(2H, s), 3.9–4.2(2H, m), 7.27(4H, s) | 405, 403 | 0.33 |
| 547 | 1.20(3H×2, d, J=6.8), 1.6–2.0(2H, m), 2.30(3H×2, s), 2.5–3.0 (10H, m), 3.42(1H, sept, J=6.8), 3.60(2H, s), 3.9–4.2(2H, m), 7.27(4H, s) | 419, 417 237 | 0.23 |
| 550 | 1.0–1.3(12H, m), 1.3–1.8(6H, m), 2.3–2.8(10H, m), 3.42(1H, sept, J=6.8), 4.0–4.3(2H, m) | 306, 112 | 0.30 |
| 551 | 0.91(3H, t, J≈6), 1.20(3H×2, d, J=6.8), 1.21(3H×2, d, J=7.6), 1.2–1.6(4H, m), 2.3–2.8(16H, m), 3.42(1H, sept, J=6.8), 4.0–4.2(2H, m) | 363, 155 | 0.25 |
| 552 | 1.20(3H×2, d, J=6.8), 1.21(3H×2, d, J=7.6), 2.3–2.8(14H, m), 3.42(1H, sept, J=6.8), 3.51(2H, s), 4.0–4.2(2H, m), 7.30(5H, s) | 397, 189 | 0.35 |
| 553 | 1.20(3H×2, d, J=6.8), 1.21(3H×2, d, J=7.6), 1.6–2.0(2H, m), 2.4–3.0(14H, m), 3.42(1H, sept, J=6.8), 3.59(2H, s), 3.80(3H, s), 3.9–4.2(2H, m), 6.84(2H, d, J=8.8), 7.24(2H, d, J=8.8) | 441, 233 | 0.21 |
| 556 | 0.94(3H×2, d, J=6.7), 1.20(3H, t, J=7.6), 1.21(3H, t, J=7.6), 2.0–2.4(1H, m), 2.4–3.0(16H, m), 3.53(2H, s), 4.0–4.3(2H, m), 7.30 (5H, s) | 411, 189 | 0.32 |
| 558 | 0.94(3H×2, d, J=6.7), 1.20(3H, t, J=7.6), 1.21(3H, t, J=7.6), 1.6–2.0(2H, m), 2.0–2.4(1H, m), 2.4–3.0(16H, m), 3.60(2H, s), 3.80(3H, s), 3.9–4.2(2H, m), 6.84(2H, d, J=8.6), 7.25(2H, d, J=8.6) | 455, 246 121 | 0.17 |
| 648 | 2.32(3H, s), 2.35(3H×2, s), 3.3–3.5(2H, m), 4.2–4.4(2H, m), 4.99 (2H, s), 8.0(1H, br. s) | 304, 302 222, 179 | |
| 649 | 2.38(3H, s), 2.43(3H, s), 2.48(3H, s), 3.6–3.8(4H, m), 4.85(2H, s), 6.8(1H, br. s) | 260, 258 | |
| 650 | 0.7–2.0(10H, m), 2.1–2.5(1H, m), 2.37(3H, s), 2.42(3H, s), 2.48 (3H, s), 2.81(2H, t, J=5.8), 3.2–3.5(3H, m), 4.84(2H, s), 7.1 (1H, br. s) | 321 | |
| 651 | 1.29(3H, t, J≈7), 2.36(3H, s), 2.41(3H, s), 2.87(2H, q, J≈7), 3.69 (3H, s), 6.14(1H, s), 7.3–7.7(5H, m) | 301, 121 | |
| 652 | 1.22(3H, t, J≈7.6), 2.31(3H, s), 2.37(3H, s), 2.83(2H, q, J≈7.6), 5.65(1H, br. s), 6.14(1H, s), 7.2–7.6(5H, m) | 287 | |
| 653 | 1.22(3H/2, t, J≈7.4), 1.27(3H/2, t, J≈7.4), 2.72(1H, q, J=7.4), 2.80(1H, q, J≈7.4), 3.2–3.5(4H, m), 4.17(2H, s), 4.81(2H, s), 6.9 (1H, br. s), 7.0–7.4(5H, m) | 364, 362 241, 146 | |
| 654 | 1.19(3H, t, J=5.7), 1.23(3H, t, J=5.7), 2.65(2H, q, J=5.7), 2.73 (2H, q, J=5.7), 3.73(3H, s), 4.16(2H, s), 4.85(2H, s), 7.0–7.5(5H, m) | 315 | |
| 655 | 1.19(3H, t, J=7.6), 1.21(3H, t, J=7.6), 2.65(2H, q, J=7.6), 2.75 (2H, q, J=7.6), 4.16(2H, s), 4.88(2H, s), 6.98(1H, br. s), 7.0–7.4 (5H, m) | 301 | |
| 656 | 1.22(3H, t, J=7.4), 1.27(3H, t, J=7.4), 2.72(2H, q, J=7.4), 2.80 (2H, q, J=7.4), 3.2–3.5(4H, m), 4.17(2H, s), 4.81(2H, s), 6.91(1H, br. s), 7.0–7.4(5H, m) | 364, 362 241, 146 | |
| 657 | 1.23(3H, t, J≈7.6), 1.26(3H, t, J≈7.6), 1.6–1.8(2H, m), 2.34 (2H×2, J≈4.7), 2.70(2H, q, J=7.6), 2.78(2H, q, J≈7.6), 3.0–3.4 (2H, m), 3.4–3.6(4H, m), 4.18(2H, s), 4.83(2H, s), 6.31(1H, br. s), 7.0–7.4(5H, m) | 413, 102 | 0.50 |
| 658 | 1.23(3H, t, J=7.6), 1.4–2.0(2H, m), 2.2–3.6(10H, m), 4.21(2H, s), 4.83(2H, s), 6.51(1H, br. s), 70.–7.4(10H, m) | 487, 174 | 0.44 |
| 662 | 1.23(3H, t, J≈7.6), 2.39(3H×2, s), 2.83(2H, q, J≈7.4), 3.75(3H, s) 4.88(2H, s) | 225 | |
| 663 | 2.33(3H, s), 2.41(3H, s), 3.73(3H, s), 4.15(2H, s), 4.87(2H, s), 7.0–7.4(5H, m) | 287 | |
| 664 | 1.27(3H×2, d, J=6.8), 2.32(3H, s), 2.40(3H, s), 3.34(1H, sept, J=6.8), 3.75(3H, s), 4.90(2H, s) | 239 | |
| 665 | 1.23(3H, t, J=7.6), 1.24(3H, t, J=7.6), 1.28(3H×2, d, J=6.8), 2.65(2H, q, J=7.6), 2.73(2H, q, J=7.6), 3.34(1H, sept, J=6.8), 3.74(3H, s), 4.87(2H, s) | 267 | 0.89 |
| 666 | 0.94(3H×2, d, J=6.7), 1.20(3H, t, J≈7.3), 1.21(3H, t, J≈7.3), 2.18 (1H, sept, J=7.3), 2.5–2.9(6H, m), 3.74(3H, s), 4.86(2H, s) | 281 | 0.68 |
| 679 | 2.38(3H, s), 2.41(3H×2, s), 3.64(1H, t, J≈5.5), 3.8–4.1(3H, m), 4.4–4.6(2H, m) | 183 | 0.59 |
| 680 | 1.23(3H, t, J≈7.4), 2.32(3H×2, s), 2.78(2H, q, J≈7.4), 3.8–4.1 (3H, m), 4.4–4.6(2H, m) | 197 | 0.64 |
| 681 | 2.38(3H, s), 2.45(3H, s), 2.6–2.8(1H, br. m), 3.7–3.9(2H, m), 4.11 (2H, s), 4.3–4.5(2H, m), 7.1–7.4(5H, m) | 259 | 0.91 |
| 682 | 1.24(3H×2, d, J≈6.8), 2.37(3H, s), 2.42(3H, s), 3.29(1H, sept, J≈6.8), 3.6–4.0(2H, m), 4.3–4.5(2H, m) | 211 | 0.57 |
| 683 | 1.1–1.4(12H, m), 2.70(2H, q, J=7.6), 3.30(1H, sept, J=6.8), 3.8–4.1(3H, m), 4.4–4.6(2H, m) | 239 | 0.63 |
| 684 | 0.93(3H×2, d, J≈6.7), 1.20(3H, t, J≈7.3), 1.26(3H, t, J≈7.3), 2.13(1H, sept, J≈7.3), 2.6–2.9(6H, m), 3.67(1H, t, J≈5.3), 3.8–4.1(3H, m), 4.4–4.6(2H, m) | 253 | 0.71 |
| 697 | 0.91(3H, t, J≈6), 1.20(3H×2, d, J=6.8), 1.2–1.6(4H, m), 2.2–2.8 (12H, m), 2.31(3H×2, q), 3.43(1H, sept, J=6.8), 4.0–4.3(2H, m) | 345 | 0.18 |
| 810 | 0.91(3H, t), 1.1–1.6(4H, m), 2.30(3H, s), 2.34(3H, s), 2.41(3H, s), 4.15(2H, t), 2.3–2.7(12H, m) | 307 | 0.26 |
| 812 | 0.91(3H, t), 1.23(3H, t), 1.1–1.6(4H, m), 2.31(6H, s), 2.3–2.9 (14H, m), 4.14(2H, t) | 321 | 0.19 |

TABLE 25-continued

NMR spectrum, Mass spectrum and Rf-value on silica-gel layer chromatography

| Comp. No. | NMR (CDCl₃, inner standard TMS) ppm | MASS | Rf |
|---|---|---|---|
| 814 | 0.91(3H, t), 1.20(6H, t), 1.1–1.7(4H, m), 2.31(6H, s), 2.3–2.9 (12H, m), 3.42(1H, sept), 4.14(2H, t) | 335 | 0.22 |
| 822 | 2.30(3H, s), 2.33(3H, s), 2.41(3H, s), 2.3–2.7(12H, m), 3.62(2H, t), 4.15(3H, t) | 295 | 0.02 |
| 825 | 1.20(6H, d), 2.31(6H, s), 2.1–2.9(12H, m), 3.42(1H, sept), 3.62 (2H, t), 4.14(2H, t) | 323 | 0.06 |
| 826 | 1.21(6H, d), 1.21(6H, t), 2.0–2.9(12H, m), 3.42(1H, sept), 3.62 (2H, t), 4.13(2H, t) | 351 | 0.04 |
| 834 | 1.20(6H, d), 1.3–1.8(6H, m), 2.31(3H, s), 2.34(3H, s), 2.4–2.7 (6H, m), 3.42(1H, sept), 4.21(2H, t) | 278 | 0.22 |
| 842 | 1.04(6H, t), 2.30(3H, s), 2.35(3H, s), 2.41(3H, s), 2.5–2.8(6H, m), 4.11(2H, t) | 238 | 0.63 |
| 844 | 1.04(6H, t), 1.23(3H, t), 2.31(3H, s), 2.34(3H, s), 2.3–2.9(8H, m), 4.11(2H, t) | 252 | 0.46 |
| 846 | 1.09(6H, t), 1.20(6H, d), 2.31(3H, s), 2.34(3H, s), 2.4–2.9(6H, m), 3.43(1H, sept), 4.14(2H, t) | 266 | 0.63 |
| 848 | 0.99–1.27(18H, m), 2.4–2.9(10H, m), 3.44(1H, sept), 4.13(2H, t) | 294 | 0.27 |

TABLE 26 physical properties of 2-hydroxy-3-substituted-5,6,7,8-tetrahydroquinoxaline

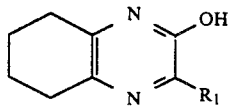

| R₁ | NMR (CDCl₃, inner standard TMS) δ ppm | MASS |
|---|---|---|
| Me | 1.78–1.84 (4H, m), 2.42 (3H, s), 2.66 (4H, m), 13.05 (1H, br, s) | 165 |
| Et | 1.25 (3H, t), 1.7–1.9 (4H, m), 2.5–2.8 (4H, m), 2.80 (2H, q), 13.06 (1H, br, s) | 179 |
| Pro | 1.00 (4H, t), 1.55 (6H, m), 2.67–2.83 (6H, m), 13.09 (1H, br, s) | 193 |
| iso-Pro | 1.24 (3H×2, d×2, J=6.8), 1.7–2.0 (4H, m), 2.5–2.8 (4H, m), 3.41 (1H, sept, J=6.8), 12.9 (1H, br, s) | 193 |
| Bu | 0.94 (3H, t), 1.24–2.00 (8H, m), 2.55–2.85 (6H, m), 12.99 (1H, br, s) | 207 |
| iso-Bu | 0.96 (3H×2, d), 1.6–2.0 (4H, m), 2.0–2.4 (1H, m), 2.5–2.8 (6H, m) | 207 |
| sec-Bu | 0.96 (3H×2, d, J=6.7), 1.6–2.2 (5H, m), 2.5–2.8 (6H, m) | 207 |
| —(CH₂)₄CH₃ | 0.90 (3H, t, J=6.3), 1.2–1.5 (4H, m), 1.5–1.9 (6H, m), 2.5–2.9 (6H, m) | 221, 164 |
| —(CH₂)₅CH₃ | 0.88 (3H, t, J=7.9), 1.1–1.5 (6H, m), 1.5–2.0 (6H, m), 2.4–2.9 (6H, m) | 235 |
| —(CH₂)₆CH₃ | 0.88 (3H, t, J≈7.4), 1.1–1.5 (8H, m), 1.5–2.0 (6H, m), 2.5–2.9 (6H, m) | 249, 164 |
| —(CH₂)₇CH₃ | 0.88 (3H, t, J=7.5), 1.1–1.5 (10H, m), 1.5–2.0 (6H, m), 2.5–2.9 (6H, m) | 263 |
| —(CH₂)₈CH₃ | 0.88 (3H, t, J=6.2), 1.1–1.5 (12H, m), 1.5–2.0 (6H, m), 2.5–2.8 (6H, m) | 277, 164 |
| —(CH₂)₉CH₃ | 0.88 (3H, t, J≈6), 1.2–2.0 (20H, m), 2.5–2.9 (6H, m), 12.7(1H, br, s) | 291 |
| —(CH₂)₁₁CH₃ | 0.88 (3H, t, J≈6), 1.1–1.9 (24H, m), 2.4–2.8 (6H, m) | 319, 164 |
| —(CH₂)₁₃CH₃ | 0.88 (3H, t, J≈6), 1.1–1.9 (28H, m), 2.5–2.8 (6H, m) | 347, 164 |
| —(CH₂)₁₅CH₃ | 0.88 (3H, t, J≈6), 1.1–1.9 (32H, m), 2.5–2.8 (6H, m) | 375, 164 |
| —CH₂Ph | 1.6–2.0 (4H, m), 2.4–2.7 (4H, m), 4.02 (2H, s), 7.0–7.4 (4H, m) | 241 |
| —CH₂CH₂Ph | 1.6–2.0 (4H, m), 2.5–2.8 (4H, m), 3.06 (2H×2, s), 7.1–7.3 (5H, s), 12.9 (1H, br, s) | 255 |

TABLE 27 physical properties of a compound of the present invention

| Comp. No. | NMR (CDCl₃, inner standard TMS) δ ppm | MASS | Rf |
|---|---|---|---|
| 368 | 1.7–2.0 (4H, m), 2.2–3.0 (14H, m), 3.0–3.6 (2H, m), 3.40 (2H, s), 4.17 (2H, s), 4.79 (2H, s), 6.4 (1H, br, s), 7.0–7.4 (10H, m) | 500, 189 | 0.45 |
| 369 | 1.6–2.0 (4H, m), 2.1–3.0 (14H, m), 3.0–3.6 (2H, m), 3.34 (2H, s), 3.79 (3H, s), 4.17 (2H, s), 4.79 (2H, s), 6.4 (1H, br, s), 6.7–7.4 (9H, m) | 530, 219 | 0.43 |
| 370 | 1.6–2.0 (4H, m), 2.1–3.0 (14H, m), 3.0–3.6 (2H, m), 3.35 (2H, s), 4.18 (2H, s), 4.79 (2H, s), 6.3 (1H, br, s), 7.0–7.4 (9H, m) | 535, 533 223 | 0.4 |
| 371 | 1.6–2.0 (4H, m), 2.3–3.0 (10H, m), 3.0–3.4 (6H, m), 4.19 (2H, s), 4.82 (2H, s), 6.4 (1H, br, s), 6.7–7.4 (9H, m) | 522, 520 209 | 0.48 |
| 372 | 1.5–2.1 (6H, m), 2.3–3.0 (14H, m), 3.0–3.4 (2H, m), 3.51 (2H, s), 4.17 (2H, s), 4.79 (2H, s), 6.3 (1H, br, s), 6.9–7.4 (9H, m) | 532, 221 | 0.38 |
| 373 | 1.6–2.1 (2H, m), 2.2–3.0 (10H, m), 3.0–3.4 (4H, m), 4.15 (2H, s), 4.81 (2H, s), 6.3 (1H, br, s), 6.6–7.4 (10H, m) | 486, 342 175 | 0.49 |
| 517 | 0.93 (3H, t, J≈6.6), 1.2–2.0 (8H, m), 2.4–3.0 (12H, m), 3.6–3.8 (4H, m), 3.9–4.2 (2H, m) | 320, 102 | 0.42 |
| 518 | 0.93 (3H, t, J≈6.6), 1.2–2.0 (8H, m), 2.4–3.0 (16H, m), 3.53 (2H, s), 3.9–4.2 (2H, m), 7.30 (5H, s) | 409, 189 | 0.41 |
| 519 | 0.93 (3H, t, J≈6.6), 1.2–2.0 (8H, m), 2.4–3.0 (16H, m), 3.47 (2H, s), 3.9–4.2 (2H, m), 7.27 (4H, s) | 445, 443 227 | 0.43 |
| 520 | 0.93 (3H, t, J≈6.6), 1.2–2.0 (10H, m), 2.4–3.0 (16H, m), 3.60 (2H, s), 3.9–4.2 (2H, m), 7.27 (4H, s) | 459, 457 237 | 0.29 |
| 521 | 0.93 (3H, t, J≈6.6), 1.2–2.0 (8H, m), 2.4–3.0 (12H, m), 3.0–3.3 (4H, m), 4.0–4.3 (2H, m), 6.7–7.4 (5H, m) | 395, 175 | 0.61 |

TABLE 27-continued physical properties of a compound of the present invention

| Comp. No. | NMR (CDCl₃, inner standard TMS) δ ppm | MASS | Rf |
|---|---|---|---|
| 522 | 0.93 (3H, t, J≈6.6), 1.2–2.0 (8H, m), 2.5–3.0 (12H, m), 3.2–3.2 (4H, m), 3.86 (3H, s), 4.0–4.3 (2H, m), 6.7–7.1 (4H, m) | 425, 205 | 0.69 |
| 559 | 0.89 (3H, t, J≈6), 1.2–2.0 (10H, m), 2.4–2.9 (12H, m), 3.6–3.8 (4H, m), 3.9–4.2 (2H, m) | 334, 102 | 0.44 |
| 560 | 0.89 (3H, t, J≈6), 0.91 (3H, t, J≈6), 1.2–2.0 (14H, m), 2.2–2.9 (18H, m), 3.9–4.2 (2H, m) | 389, 155 | 0.24 |
| 561 | 0.89 (3H, t, J≈6), 1.1–2.0 (10H, m), 2.4–2.9 (16H, m), 3.53 (2H, s), 3.9–4.2 (2H, m), 7.30 (5H, s) | 423, 189 | 0.31 |
| 562 | 0.89 (3H, t, J≈6), 1.1–2.0 (12H, m), 2.4–2.9 (16H, m), 3.61 (2H, s), 3.9–4.2 (2H, m), 6.8–8.4 (4H, m) | 455, 234 221 | 0.19 |
| 563 | 0.89 (3H, t, J≈6), 1.2–2.0 (10H, m), 2.5–2.9 (12H, m), 3.0–3.2 (4H, m), 3.86 (3H, s), 4.0–4.3 (2H, m), 6.7–7.1 (4H, m) | | |
| 564 | 0.87 (3H, t, J≈6), 1.1–2.0 (12H, m), 2.4–2.9 (12H, m), 3.6–3.8 (4H, m), 3.9–4.2 (2H, m) | 348, 101 | 0.32 |
| 565 | 0.87 (3H, t, J≈6), 0.91 (3H, t, J≈6), 1.1–2.0 (16H, m), 2.1–2.9 (18H, m), 3.9–4.2 (2H, m) | 403, 155 | 0.20 |
| 567 | 0.87 (3H, t, J≈6), 1.1–2.0 (12H, m), 2.3–2.9 (16H, m), 3.52 (2H, s), 2.9–4.2 (2H, m), 7.30 (5H, s) | 437, 189 | 0.28 |
| 568 | 0.87 (3H, t, J≈6), 1.1–2.0 (12H, m), 2.4–2.9 (16H, m), 3.52 (2H, s), 3.9–4.2 (2H, m), 7.30 (4H, s) | 473, 471 236, 223 | 0.31 |
| 569 | 0.87 (3H, t, J≈6), 1.1–2.0 (14H, m), 2.4–3.0 (16H, m), 3.60 (2H, s), 3.9–4.2 (2H, m), 6.8–7.4 (4H, m) | 469, 234 221 | 0.20 |
| 570 | 0.87 (3H, t, J≈6), 1.1–2.0 (12H, m), 2.5–3.0 (12H, m), 2.9–3.2 (4H, 3.86 (3H, s), 4.0–4.3 (2H, m), 6.7–7.1 (4H, m) | 453, 218 205 | 0.53 |
| 571 | 0.7–1.0 (6H, m), 1.1–2.0 (18H, m), 2.2–2.9 (18H, m), 3.9–4.2 (2H, m) | 417, 155 | 0.33 |
| 572 | 0.87 (3H, t, J≈6), 1.1–2.0 (16H, m), 2.4–2.9 (12H, m), 3.6–3.8 (4H, m), 3.9–4.2 (2H, m) | 376 | 0.58 |
| 573 | 0.7–1.0 (6H, m), 1.1–2.0 (20H, m), 2.2–2.9 (18H, m), 3.9–4.2 (2H, m) | 431, 155 | 0.27 |
| 574 | 0.87 (3H, t, J≈6), 1.1–2.0 (16H, m), 2.4–2.9 (16H, m), 3.53 (2H, s), 3.9–4.2 (2H, m), 7.30 (5H, s) | 465, 189 | 0.52 |
| 575 | 0.87 (3H, t, J≈6), 1.1–2.0 (16H, m), 2.3–2.9 (16H, m), 3.9–4.2 (2H, m), 7.26 (4H, s) | 501, 499 223 | 0.43 |
| 576 | 0.87 (3H, t, J≈6), 1.1–2.0 (18H, m), 2.5–2.9 (16H, m), 3.59 (2H, s), 3.9–4.2 (2H, m), 6.8–7.4 (4H, m) | 497, 235 221 | 0.24 |
| 577 | 0.88 (3H, t, J≈6), 1.1–2.0 (16H, m), 2.5–2.9 (12H, m), 3.0–3.3 (4H, m), 4.0–4.3 (2H, m), 6.7–7.4 (5H, m) | 450, 189 175 | 0.67 |
| 578 | 0.87 (3H, t, J≈6), 1.1–2.0 (16H, m), 2.5–2.9 (12H, m), 3.0–3.2 (4H, m), 3.77 (3H, s), 4.0–4.2 (2H, m), 6.86 (4H, s) | 480, 218 205 | 0.55 |
| 579 | 0.87 (3H, t, J≈6), 1.0–2.0 (18H, m), 2.4–2.9 (12H, m), 3.5–3.8 (4H, m), 3.9–4.2 (2H, m) | 390, 102 | 0.39 |
| 580 | 0.87 (3H, t, J≈6), 0.91 (3H, t, J≈6), 1.0–2.0 (22H, m), 2.3–2.9 (18H, m), 3.9–4.2 (2H, m) | 445, 155 | 0.29 |
| 581 | 0.87 (3H, t, J≈6), 1.0–2.0 (18H, m), 2.4–2.9 (16H, m), 3.52 (2H, s), 3.9–4.2 (2H, m) | 479, 202 189 | 0.32 |
| 582 | 0.87 (3H, t, J≈6), 1.0–2.0 (18H, m), 2.3–2.9 (16H, m), 3.47 (2H, s), 3.80 (3H, s), 3.9–4.2 (2H, m), 6.84 (2H, d, J=8.8), 7.23 (2H, d, J=8.8) | 509, 232 219 | 0.28 |
| 583 | 0.87 (3H, t, J≈6), 1.0–2.0 (20H, m), 2.4–3.0 (16H, m), 3.59 (2H, s), 3.9–4.2 (2H, m), 7.26 (4H, s) | 529, 527 250, 237 | 0.39 |
| 584 | 0.87 (3H t, J≈6), 1.0–2.0 (18H, m), 2.4–2.9 (12H, m), 3.0–3.2 (4H, m), 3.9–4.2 (2H, m), 6.7–7.3 (4H, m) | 501, 499 222, 209 | 0.46 |
| 585 | 0.87 (3H, t, J≈6), 1.0–2.0 (20H, m), 2.4–2.9 (12H, m), 3.5–3.8 (4H, m), 3.9–4.2 (2H, m) | 404, 113 102 | 0.37 |
| 586 | 0.87 (3H, t, J≈6), 1.0–2.0 (26H, m), 2.4–2.9 (12H, m), 4.0–4.3 (4H, m) | 402, 112 | 0.29 |
| 587 | 0.87 (3H, t, J≈6), 0.91 (3H, t, J≈6), 1.0–2.0 (24H, m), 2.2–2.9 (18H, m), 3.9–4.2 (2H, m) | 459, 155 125 | 0.26 |
| 588 | 0.87 (3H, t, J≈6), 1.0–2.0 (20H, m), 2.3–2.9 (18H, m), 3.62 (2H, t, J≈6), 3.9–4.2 (2H, m) | 447, 156 143, 125 | 0.12 |
| 589 | 0.87 (3H, t, J≈6), 1.0–2.0 (20H, m), 2.4–2.9 (16H, m), 3.52 (2H, s), 3.9–4.2 (2H, m), 7.30 (5H, s) | 493, 202 189 | 0.37 |
| 590 | 0.87 (3H, t, J≈6), 1.0–2.0 (20H, m), 2.3–2.9 (16H, m), 3.52 (2H, s), 3.9–4.2 (2H, m), 7.26 (4H, s) | 529, 527 236, 223 125 | 0.41 |
| 591 | 0.87 (3H, t, J≈6), 1.0–2.0 (20H, m), 2.3–2.9 (16H, m), 3.8–4.2 (2H, m), 4.22 (1H, s), 7.0–7.6 (10H, m) | 569, 278 167 | 0.66 |
| 592 | 0.87 (3H, t, J≈6), 1.0–2.0 (22H, m), 2.4–3.0 (16H, m), 3.60 (2H, s), 3.9–4.2 (2H, m), 6.8–7.4 (4H, m) | 525, 234 221 | 0.27 |
| 593 | 0.87 (3H, t, J≈6), 1.0–2.0 (20H, m), 2.4–2.9 (12H, m), 2.9–3.2 (4H, m), 3.77 (4H, s), 3.9–4.2 (2H, m), 6.6–7.0 (4H, m) | 509, 218 205 | 0.60 |
| 594 | 0.88 (3H, t, J≈6), 1.0–2.0 (24H, m), 2.4–3.0 (12H, m), 3.6–3.8 (4H, m), 3.9–4.2 (2H, m) | 432, 101 | 0.34 |
| 595 | 0.88 (3H, t, J≈6), 0.91 (3H, t, J≈6), 1.0–2.0 (28H, m), 2.2–3.0 (18H, m), 3.9–4.2 (2H, m) | 487, 155 | 0.16 |
| 596 | 0.88 (3H, t, J≈6), 1.0–2.0 (24H, m), 2.3–2.9 (16H, m), 3.53 (2H, s), 3.9–4.2 (2H, m), 7.30 (5H, s) | 521, 202 179 | 0.21 |
| 597 | 0.88 (3H, t, J≈6), 1.0–2.0 (24H, m), 2.4–2.9 (16H, m), 3.47 (2H, s), 3.79 (3H, s), 3.9–4.2 (2H, m), 6.84 (2H, d, J≈8.6), 7.22 (2H, d, J=8.6) | 551, 232 219 | 0.21 |
| 598 | 0.88 (3H, t, J≈6), 1.0–2.0 (26H, m), 2.4–3.0 (16H, m), 3.9–4.2 (2H, m), 6.8–7.4 (4H, m) | 553, 234 221 | 0.15 |
| 599 | 0.88 (3H, t, J≈6), 1.0–2.0 (24H, m), 2.5–2.9 (12H, m), 2.9–3.2 (4H, | 537, 208 | 0.43 |

TABLE 27-continued physical properties of a compound of the present invention

| Comp. No. | NMR (CDCl₃, inner standard TMS) δ ppm | MASS | Rf |
|---|---|---|---|
| | m), 3.86 (3H, s), 3.9-4.1 (2H, m), 6.7-7.1 (2H, m) | 205 | |
| 600 | 0.88 (3H, t, J≈6), 0.91 (3H, t, J≈6), 1.0-2.0 (32H, m), 2.2-2.9 (18H, m), 3.9-4.2 (2H, m) | 515, 155 | 0.22 |
| 601 | 0.88 (3H, t, J≈6), 1.0-2.0 (28H, m), 2.4-2.9 (16H, m), 3.51 (2H, s), 3.9-4.2 (2H, m), 7.29 (5H, s) | 549, 202 189 | 0.36 |
| 602 | 0.88 (3H, t, J≈6), 1.0-2.0 (28H, m), 2.3-2.9 (16H, m), 3.47 (2H, s), 3.9-4.2 (2H, m), 6.8-7.4 (4H, m) | 567, 549 220, 207 | 0.37 |
| 603 | 0.88 (3H, t, J≈6), 1.0-2.0 (30H, m), 2.4-3.0 (16H, m), 3.60 (2H, s), 3.9-4.2 (2H, m), 7.27 (4H, s) | 599, 597 250 | 0.30 |
| 604 | 0.88 (3H, t, J≈6), 1.0-2.0 (28H, m), 2.3-2.9 (16H, m), 3.9-4.2 (2H, m), 4.23 (1H, s), 7.0-7.5 (10H, m) | 625, 228 167 | 0.71 |
| 605 | 0.88 (3H, t, J≈6), 1.0-2.0 (28H, m), 2.5-3.0 (12H, m), 2.9-3.2 (4H, m), 4.0-4.3 (2H, m), 6.8-7.4 (4H, m) | 571, 569 222, 209 | 0.71 |
| 606 | 0.88 (3H, t, J≈6), 1.0-2.0 (28H, m), 2.4-2.9 (12H, m), 3.5-3.8 (4H, m), 3.9-4.2 (2H, m) | 488, 113 | 0.47 |
| 607 | 0.88 (3H, t, J≈6), 0.91 (3H, t, J≈6), 1.0-2.0 (36H, m), 2.1-2.8 (18H, m), 3.9-4.2 (2H, m) | 543, 168 155 | 0.26 |
| 608 | 0.88 (3H, t, J≈6), 1.0-2.0 (32H, m), 2.3-2.9 (16H, m), 3.51 (2H, s), 3.9-4.2 (2H, m), 7.29 (5H, s) | 578, 202 | 0.35 |
| 609 | 0.88 (3H, t, J≈6), 1.0-2.0 (34H, m), 2.5-2.9 (16H, m), 3.62 (2H, s), 3.80 (3H, s), 3.9-4.2 (2H, m), 6.84 (2H, d, J=8.6), 7.26 (2H, d, J=8.6) | 621, 246 121 | 0.25 |
| 610 | 0.88 (3H, t, J≈6), 1.0-2.0 (32H, m), 2.4-2.9 (12H, m), 2.9-3.2 (4H, m), 3.76 (3H, s), 3.9-4.2 (2H, m), 6.6-7.0 (4H, m) | 592, 218 | 0.45 |
| 659 | 1.7-1.9 (4H, m), 2.6-2.9 (4H, m), 3.73 (3H, s), 4.16 (2H, s), 4.86 (2H, s), 7.0-7.4 (5H, m) | 313 | |
| 660 | 1.7-1.9 (4H, m), 2.6-3.0 (4H, m), 4.16 (2H, s), 4.87 (2H, s), 7.0-7.5 (5H, m) | 299 | |
| 661 | 1.7-1.9 (4H, m), 2.6-2.9 (4H, m), 3.2-3.5 (4H, m), 4.17 (2H, s), 4.85 (2H, s), 7.0-7.5 (5H, m) | 362, 360 | |
| 667 | 0.94 (3H, t, J≈7.4), 1.2-2.0 (8H, m), 2.6-3.0 (6H, m), 3.75 (3H, s), 4.88 (2H, s) | 279 | 0.89 |
| 668 | 0.89 (3H, t, J≈6), 1.2-2.0 (10H, m), 2.6-3.0 (6H, m), 3.75 (3H, s), 4.89 (2H, s) | 293 | 0.90 |
| 669 | 0.88 (3H, t, J≈6), 1.2-2.0 (12H, m), 2.6-3.0 (6H, m), 3.75 (3H, s), 4.88 (2H, s) | 307 | 0.92 |
| 670 | 0.88 (3H, t, J≈6), 1.2-2.0 (14H, m), 2.6-3.0 (6H, m), 3.75 (3H, s), 4.89 (2H, s) | 321 | 0.93 |
| 671 | 0.87 (3H, t, J≈6), 1.2-2.0 (16H, m), 2.6-3.0 (6H, m), 3.75 (3H, s), 4.88 (2H, s) | 335 | 0.93 |
| 672 | 0.87 (3H, t, J≈6), 1.1-2.0 (18H, m), 2.6-3.0 (6H, m), 3.75 (3H, s), 4.88 (2H, s) | 349 | 0.93 |
| 673 | 0.87 (3H, t, J≈6), 1.1-2.0 (20H, m), 2.6-3.0 (6H, m), 3.75 (3H, s), 4.88 (2H, s) | 363 | 0.94 |
| 674 | 0.87 (3H, t, J≈6), 1.1-2.0 (24H, m), 2.6-3.0 (6H, m), 3.75 (3H, s), 4.88 (2H, s) | 391 | 0.94 |
| 675 | 0.88 (3H, t, J≈6), 1.0-2.0 (28H, m), 2.6-3.0 (6H, m), 3.75 (3H, s), 4.88 (2H, s) | 419 | 0.94 |
| 676 | 0.88 (3H, t, J≈6), 1.0-2.0 (32H, m), 2.6-3.0 (6H, m), 3.75 (3H, s), 4.88 (2H, s) | 447 | 0.95 |
| 677 | 0.99 (3H, t, J=7.3), 1.5-2.0 (6H, m), 3.75 (3H, s), 3.89 (2H, s) | 265 | 0.86 |
| 678 | 0.86 (3H, t, J=7.4), 1.25 (2H, d, J=7.8), 1.6-2.0 (6H, m), 2.6-2.9 (4H, m), 2.9-3.3 (1H, m), 3.74 (3H, s), 4.88 (2H, s) | 2.79 | 0.88 |
| 685 | 0.93 (3H, t, J≈6.7), 1.1-2.0 (8H, m), 2.6-3.0 (6H, m), 3.6-4.1 (3H, m), 4.4-4.6 (2H, m) | 251 | 0.66 |
| 686 | 0.89 (3H, t, J≈6), 1.2-2.0 (10H, m), 2.6-3.0 (6H, m), 3.7 (1H, br, s), 3.8-4.1 (2H, m), 4.4-4.6 (2H, m) | 265 | 0.67 |
| 687 | 0.88 (3H, t, J≈6), 1.0-2.0 (12H, m), 2.6-3.0 (6H, m), 3.7 (1H, br, s), 3.8-4.1 (2H, m), 4.3-4.6 (2H, m) | 279 | 0.67 |
| 688 | 0.88 (3H, t, J≈6), 1.2-2.0 (14H, m), 2.6-3.0 (6H, m), 3.7 (1H, br, s), 3.8-4.1 (2H, m), 4.4-4.6 (2H, m) | 293 | 0.67 |
| 689 | 0.88 (3H, t, J≈6), 1.1-2.0 (16H, m), 2.6-3.0 (6H, m), 3.7 (1H, br, s), 3.8-4.1 (2H, m), 4.4-4.6 (2H, m) | 307 | 0.69 |
| 690 | 0.87 (3H, t, J≈6), 1.0-2.0 (18H, m), 2.6-3.0 (6H, m), 3.7 (1H, br, s), 3.8-4.1 (2H, m), 4.4-4.6 (2H, m) | 321 | 0.70 |
| 691 | 0.88 (3H, t, J≈6), 1.1-2.0 (20H, m), 2.6-3.0 (6H, m), 3.7-4.1 (3H, m), 4.4-4.6 (2H, m) | 335 | 0.72 |
| 692 | 0.88 (3H, t, J≈6), 1.0-2.0 (24H, m), 2.6-3.0 (6H, m), 3.7-4.1 (3H, m), 4.4-4.6 (2H, m) | 363 | 0.78 |
| 693 | 0.88 (3H, t, J≈6), 1.0-2.0 (28H, m), 2.5-3.0 (6H, m), 3.7-4.1 (3H, m), 4.4-4.6 (2H, m) | 391 | 0.81 |
| 694 | 0.88 (3H, t, J≈6), 1.0-2.0 (32H, m), 2.6-3.0 (6H, m), 3.7-4.1 (3H, m), 4.3-4.6 (2H, m) | 419 | 0.81 |
| 695 | 0.97 (3H, t, J=7.3), 1.5-2.0 (6H, m), 2.6-3.0 (6H, m), 3.7 (1H, br, s), 3.8-4.1 (2H, m), 4.4-4.6 (2H, m) | 237 | 0.54 |
| 696 | 0.84 (3H, t, J=7.4), 1.21 (3H, d, J≈7), 1.2-2.0 (6H, m), 2.6-2.9 (6H, m), 2.8-3.3 (1H, m), 3.8-4.1 (3H, m), 4.3-4.5 (2H, m) | 251 | 0.65 |
| 817 | 0.91 (3H, t), 0.93 (3H, t), 1.1-1.9 (12H, m), 2.0-3.0 (18H, m), 4.08 (2H, t) | 375 | 0.22 |
| 830 | 0.87 (3H, t), 1.1-1.5 (10H, m), 1.5-2.0 (6H, m), 2.4-2.9 (18H, m), 3.63 (2H, t), 4.09 (2H, t) | 419 | 0.23 |

TABLE 27-continued

| | physical properties of a compound of the present invention | | |
|---|---|---|---|
| Comp. No. | NMR (CDCl$_3$, inner standard TMS) δ ppm | MASS | Rf |
| 837 | 0.93 (3H, t), 1.0–2.0 (14H, m), 2.0–3.0 (12H, m), 4.11 (3H, t) | 318 | 0.28 |
| 839 | 0.87 (3H, t), 1.1–2.0 (22H, m), 2.4–2.9 (12H, m), 4.12 (2H, t) | 274 | 0.30 |
| 850 | 0.93 (3H, t), 1.06 (6H, t), 1.1–2.0 (8H, m), 2.4–3.0 (12H, m), 4.08 (2H, t) | 306 | 0.69 |
| 851 | 0.87 (3H, t), 1.04 (6H, t), 1.2–1.5 (10H, m), 1.5–2.0 (6H, m), 2.5–3.0 (12H, m), 4.06 (2H, t) | 362 | 0.19 |

What is claimed is:

1. A compound of the formula

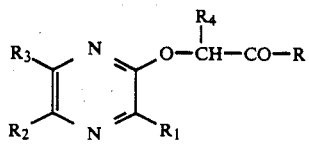

wherein R is hydroxyl, lower alkoxy, —NH—lower alkylene—OH, —NH—lower alkylene-arylthio,

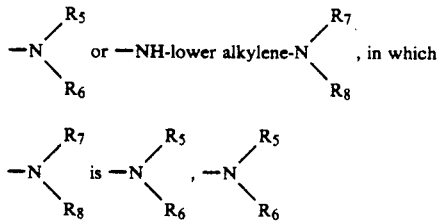

$R_1$ is di-lower alkylamino, morpholino,

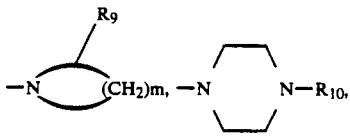

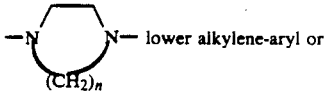

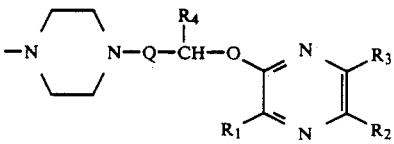

in which $R_9$ is hydrogen, lower alkyl or aryl, $R_{10}$ is hydrogen, lower alkyl, hydroxy-lower alkyl or hydroxy-lower alkoxy-lower alkyl, m is an integer from 4 to 6, n is 2 or 3, Rhd 1 is alkyl or aryl-lower alkyl, $R_2$ and $R_3$ are each lower alkyl, and $R_4$ is hydrogen, lower alkyl or aryl, in which aryl is phenyl which is optionally substituted with a group selected from the group consisting of 1–3 halogen, nitro, lower alkyl and lower alkoxy, or a pharmaceutically acceptable salt thereof.

2. A compound of the formula

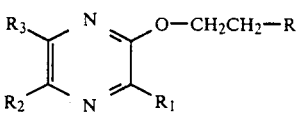

wherein R is hydroxyl or

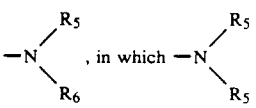

is di-lower alkylamino, morpholino,

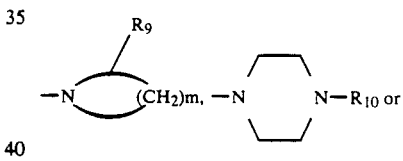

in which $R_9$ is hydrogen, lower alkyl or aryl, $R_{10}$ is hydrogen, lower alkyl, hydroxy-lower alkyl or hydroxy-lower alkoxy-lower alkyl, m is an integer from 4 to 6, n is 2 or 3, $R_1$ is alkyl or aryl-lower alkyl, $R_2$ and $R_3$ are each lower alkyl, and $R_4$ is hydrogen, lower alkyl or aryl, in which aryl is phenyl which is optionally substituted with a group selected from the group consisting of 1–3 halogen, nitro, lower alkyl and lower alkoxy, or a pharmaceutically acceptable salt thereof.

* * * * *